US007153659B2

(12) United States Patent
Harding et al.

(10) Patent No.: US 7,153,659 B2
(45) Date of Patent: Dec. 26, 2006

(54) HPV CD8+ T-CELL EPITOPES

(75) Inventors: Fiona Harding, Santa Clara, CA (US); Jeanette Marie Mucha, San Carlos, CA (US)

(73) Assignee: Genencor International, Inc., Palo Alto, CA (US)

( * ) Notice: Subject to any disclaimer, the term of this patent is extended or adjusted under 35 U.S.C. 154(b) by 0 days.

(21) Appl. No.: 10/924,377

(22) Filed: Aug. 23, 2004

(65) Prior Publication Data

US 2005/0181458 A1 Aug. 18, 2005

Related U.S. Application Data

(60) Provisional application No. 60/500,452, filed on Sep. 5, 2003.

(51) Int. Cl.
*C12Q 1/68* (2006.01)
(52) U.S. Cl. .................. 435/6; 435/325; 435/235.1
(58) Field of Classification Search ................ 435/6, 435/325, 235.1, 435
See application file for complete search history.

(56) References Cited

U.S. PATENT DOCUMENTS

| | | | |
|---|---|---|---|
| 4,683,195 A | 7/1987 | Mullis et al. ................ 435/6 |
| 4,683,202 A | 7/1987 | Mullis .......................... 435/91 |
| 4,722,848 A | 2/1988 | Paoletti et al. ............... 424/89 |
| 4,965,188 A | 10/1990 | Mullis et al. ................ 435/6 |
| 5,580,859 A | 12/1996 | Felgner et al. ................ 514/44 |
| 5,589,466 A | 12/1996 | Felgner et al. ................ 514/44 |
| 5,679,647 A | 10/1997 | Carson et al. ................ 514/44 |
| 5,736,524 A | 4/1998 | Content et al. ............... 514/44 |
| 5,739,118 A | 4/1998 | Carrano et al. ............... 514/44 |
| 5,804,566 A | 9/1998 | Carson et al. ................ 514/44 |
| 5,922,687 A | 7/1999 | Mann et al. ................... 514/44 |
| 6,962,790 B1 * | 11/2005 | Ennis ....................... 435/7.24 |
| 2001/0055752 A1 | 12/2001 | Ennis .......................... 435/4 |
| 2002/0137720 A1 | 9/2002 | Ertl et al. ..................... 514/45 |
| 2002/0187131 A1 | 12/2002 | Hawiger et al. ............. 424/93.7 |

FOREIGN PATENT DOCUMENTS

WO  WO 98/04720  2/1998

OTHER PUBLICATIONS

International Search Report for PCT/US04/27263 filed Aug. 23, 2004.
Addo, M. M. et al., "Comprehensive Epitope Analysis of Human Immunodeficiency Virus Type 1 (HIV-1)-Specific T-Cell Responses Directed against the Entire Expressed HIV-1 Genome Demonstrate Broadly Directed Responses, but No Correlation to Viral Load," *Journal of Virology*, 77(3):2081-2092, 2003.
Allen, P. M. et al., "T-Cell Recognition of Lysozyme: The Biochemical Basis of Presentation," *Immunological Reviews*, 98:171-187, 1987.
Alonso, M. J. et al., "Biodegradable microspheres as controlled-release tetanus toxoid delivery systems," *Vaccine*, 12(4):299-306, 1994.
Altman, J. D. et al., "Phenotypic Analysis of Antigen-Specific T Lymphocytes," *Science*, 274:94-96, 1996.
Altschul, S. F. et al., "Basic Local Alignment Search Tool," *J. Mol. Bio.*, 215:403-410, 1990.
Altschul, S. F. et al., "Local Alignment Statistics," *Methods in Enzymology*, 266:460-480, 1996.
Bennett, S. R. M. et al., "Help for cytotoxic-T-cell responses is mediated by CD40 signalling," *Nature*, 393:478-480, 1998.
Chakrabarti, S. et al., "Expression of the HTLV-III envelope gene by a recombinant vaccinia virus," *Nature*, 320:535-546, 1986.
Chamberlin M. et al., "New RNA Polymerase from *Escherichia coli* infected with Bacteriophage T7," *Nature*, 228:227-231, 1970.
Chanda, P. K. et al., "High Level Expression of the Envelope Glycoproteins of the Human Immunodeficiency Virus Type I in Presence of rev Gene Using Helper-Independent Adenovirus Type 7 Recombinants," *Virology*, 175:535-547, 1990.
Devereux, J. et al., "A comprehensive set of sequence analysis programs for the VAX," *Nucleic Acids Research*, 12(1):387-395, 1984.
De Veerman, M. et al., "Retrovirally Transduced Bone Marrow-Derived Dendritic Cells Require CD4+ T Cell Help to Elicit Protective and Therapeutic Antitumor Immunity," *J. Immunol.*, 162:144-151, 1999.
**Dictionary of Microbiology and Molecular Biology*, 2d Ed. John Wiley and Sons, NY, 1994.
Eldridge, J. H. et al., "Biodegradable Microspheres as a Vaccine Delivery System," *Molecular Immunology*, 28(3):287-294, 1991.
Eldridge, J. H. et al., "New Advances in Vaccine Delivery Systems," *Seminars in Hematology*, 30(4):16-25, 1993.
Erratum at *Science*, 280:1821, 1998.
Falo, L. D. et al., "Targeting antigen into the phagocytic pathway *in vivo* induces protective tumour immunity," *Nature Medicine*, 1(7):649-653, 1995.

(Continued)

*Primary Examiner*—Ali R. Salimi
(74) *Attorney, Agent, or Firm*—Genencor International, Inc.

(57) ABSTRACT

The present invention provides means to identify functional CD8+ T-cell epitopes in any protein of interest. The present invention further provides CD8+ T-cell epitopes of various proteins. In additional embodiments, the present invention provides epitopes suitable for use in prophylactic and/or therapeutic vaccines. In particularly preferred embodiments, the present invention provides modified epitopes suitable for use in prophylactic and/or therapeutic vaccines.

Figure 1:
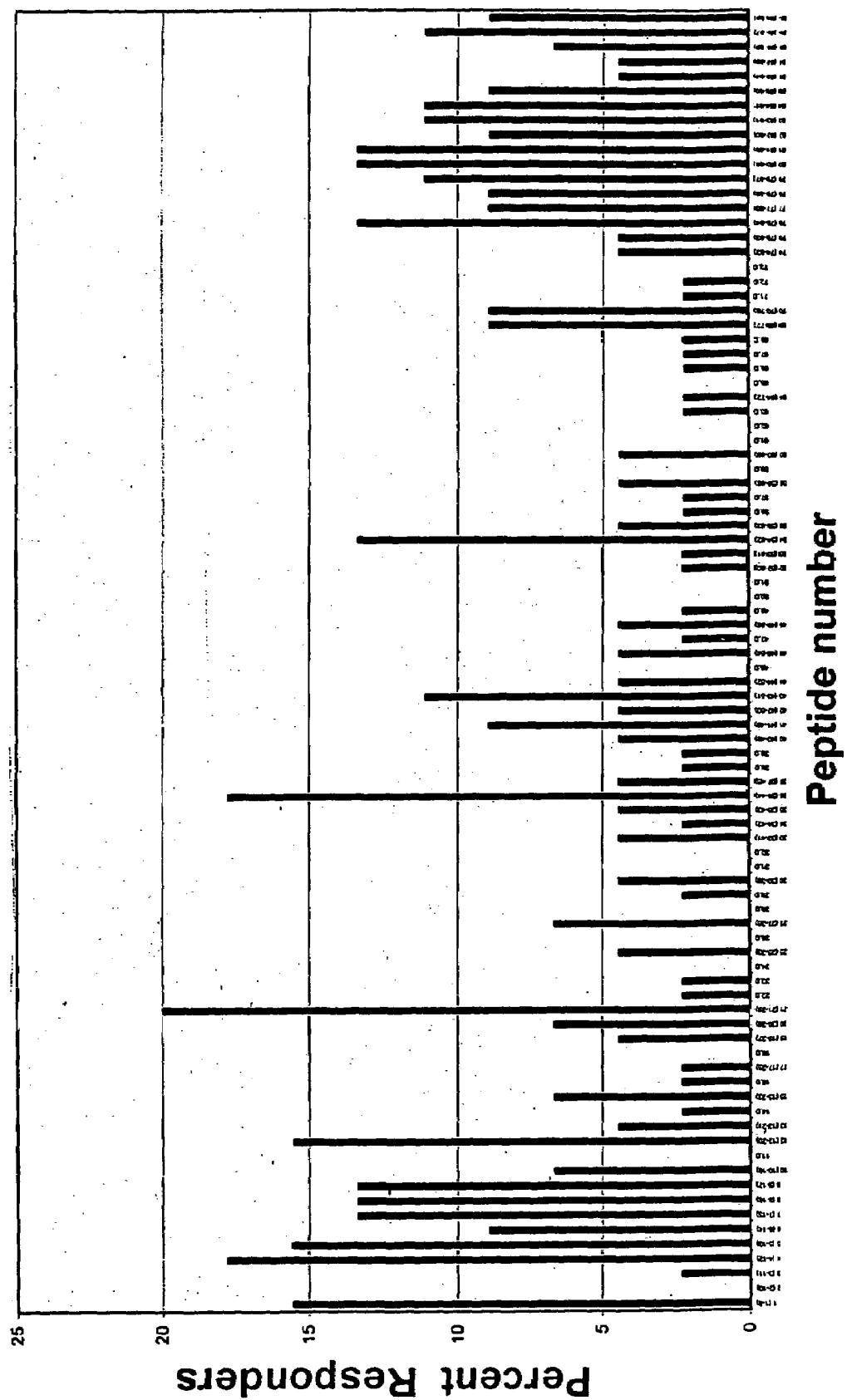

In some preferred embodiments, the present invention provides means for the development of HPV vaccines, in particular multivalent vaccines for the prevention of infection with high-risk HPV strains. In particular, the present invention provides means to identify CD8+ T-cell epitopes in HPV strains such as HPV 16 and HPV 18. In additional embodiments, the present invention provides means for the development of therapeutic vaccines against high-risk HPV types that prevent the development of benign and/or malignant tumors in infected individuals. The present invention further provides epitopes suitable for use in prophylactic and therapeutic vaccines.

2 Claims, 4 Drawing Sheets

OTHER PUBLICATIONS

Feng, Da-Fei, "Progressive Sequence Alignment as a Prerequisite to Correct Phylogenetic Trees," *Journel of Molecular Evolution*, 25:351-360 (1987).

Finzer, P. et al., "The role of human papillomavirus oncoproteins E6 and E7 in apoptosis," *Cancer Letters*, 188:15-24, 2002.

**Hale and Marham, *The Harper Collins Dictionary of Biology*, Harper Perennial, NY, 1991.

Henikoff, S. et al., "Amino acid substitution matrices from protein blocks," *Proc. Natl. Acad. Sci. USA*, 89:10915-10919, 1992.

Gupta, R. K. et al., "Adjuvants—a balance between toxicity and adjuvanticity," *Vaccine*, 11(3):293-306, 1993.

Higgins, D. G. et al., "CLUSTAL: a package for performing multiple sequence alignment on a microcomputer," *Gene*, 73:237-244, 1988.

Higgins, D. G. et al., "Fast and sensitive multiple sequence alignments on a microcomputer," *Cabios Communications*, 5(2):151-153, 1989.

Hu, K.-F. et al., "The immunostimulating complex (ISCOM) is an efficient mucosal delivery system for respiratory syncytial virus (RSV) envelope antigens inducing high local and systemic antibody responses," *Clin. Exp. Immunol.*, 113:235-243, 1998.

Hu, Shiu-Lok et al., "Expression of AIDS virus envelope gene in recombinant vaccinia viruses," *Nature*, 320:537-543, 1986.

Jones, D. H. et al., "Protection of mice from *Bordetella pertussis* respiratory infection using microencapsulated pertussis fimbriae," *Vaccine*, 13(7):675-681, 1995.

Kacian, D. L. et al., "A Replicating RNA Molecule Suitable for a Detailed Analysis of Extracellular Evolution and Replication," *Proc. Nat. Acad. Sci. USA*, 69(10):3038-3042, 1972.

Kieny, M. P. et al., "Aids Virus ENV protein Expressed From a Recombinant Vaccinia Virus," *Bio/Technology*, 4:790-795, 1988.

Kofler, N. et al., Preparation and characterization of poly-(D,L-lactide-co-glycolide) and poly-(L-lactic acid) microspheres with entrapped pneumotropic baterial antigens, *Journal of Immunological Methods*, 192:25-35, 1996.

Lorincz, A. T., "Human Papillomavirus Infection of the Cervix: Relative Resk Associations of 15 Common Anogenital Types," *Obstetrics & Gynecology*, 79(3):328-337, 1992.

Maeji, N. J. et al., "Multi-pin peptide synthesis strategy for T cell determinant analysis," *Journal of Immunological Methods*, 134:23-33, 1990.

Nakagawa, M. et al., "Cytotoxic T Lymphocyte Responses to E6 and E7 Proteins of Human Papillomavirus Type 16: Relationship to Cervical Intraepithelial Neoplasia," *Journal of Infectious Diseases*, 175:927-931, 1997.

Needleman, S. B. et al., "A General Method Applicable to the Search for Similarities in the Amino Acid Sequence of Two Proteins," *J. Mol. Biol.*, 48:443-453, 1970.

Nussbaum, A. K. et al., "Using the World Wide Web for predicting CTL epitopes," *Current Opinion in Immunology*, 15:69-74, 2003.

Osen, W. et al., "A DNA vaccine based on a shuffled E7 oncogene of the human papillomavirus type 16 (HPV 16) induces E7-specific cytotoxic T cells but lacks transforming activity," *Vaccine*, 19:4276-4286, 2001.

Ossendorp, F. et al., "Specific T Helper Cell Requirement for Optimal Induction of Cytotoxic T Lymphocytes against Major Histocompatibility Complex Class II Negative Tumors," *J. Exp. Med.*, 187(5):693-702, 1998.

Pearson, W. R. et al., "Improved tools for biological sequence comparison," *Proc. Natl. Acad. Sci. USA*, 85:2444-2448, 1988.

Perkus, M. E. et al., "Recombinant Virus as Vaccination Carrier of Heterologous Antigens," *Concepts in Vaccine Development*, Kaufinann (ed.), 1996.

Reddy, R. et al., "In Vivo Cytotoxic T Lymphocyte Induction with Soluble Proteins Administered in Liposomes," *The Journal of Immunology*, 148(5):1585-1589, 1992.

Ridge, J. P. et al., "A conditioned dendritic cell can be a temporal bridge between a CD4$^+$ T-helper and T-killer cell," *Nature*, 393:474-478.

Rock, K. L. et al., "A new foreign policy: MHC class I molecules monitor the outside world," *Immunology Today*, 17(3):131-137, 1996.

Robinson, H. L. et al., "Protection against a lethal influenza virus challenge by immunization with a haemagglutinin-expressing plasmid DNA," *Vaccine*, 11(9):957-960, 1993.

**Sambrook, et al., Molecular Cloning: A Laboratory Manual (Second Edition), Cold Spring Harbor Press, Plainview, N.Y., 1989.

Sato, Y. et al., "Improved generation of HLA class I/peptide tetramers," *Journal of Immunological Methods*, 271:177-184, 2002.

Schimke, R. T. et al., "Gene Amplification and Drug Resistance in Cultured Murine Cells," *Science*, 202:1051-1055, 1978.

Schoenberger, S. P. et al., "T-cell help for cytotoxic T lymphocytes is mediated by CD40-CD40L Interactions," *Nature*, 393:480-483, 1998.

Shiver, J. W. et al., Naked DNA "Vaccination," *Concepts in Vaccine Development*, Kaufinann (ed) p. 423-424, 1996.

Stover, C. K. et al., "New use of BCG for recombinant vaccines," *Nature*, 351:456-460, 1991.

Smith, T. F. et al., "Comparison of Biosequences," *Advances in Applied Mathematics*, 2:482-489, 1981.

Takahashi, H. et al., "Induction of CD8$^+$ Cytotoxic T cells by immunization with purified HIV-1 envelope protein in ISCOMs," *Nature*, 344:873-875, 1990.

Tam, J. P., "Synthetic peptide vaccine design: Synthesis and properties of a high-density multiple antigenic peptide system," *Proc. Natl. Acad. Sci. USA*, 85:5409-5413, 1988.

Tam, J. P., "Recent advances in multiple antigen peptides," *Journal of Immunological Methods*, 196:17-32, 1996.

Top, F. H. et al., "Immunization with Live Types 7 and 4 Adenovirus Vaccines. I. Safety, Infectivity, Antigenicity, and Potency of Adenovirus Type 7 Vaccine in Humans," *The Journal of Infectious Diseases*, 124(2):148-154, 1971.

Terajima, M. et al., "Quantitation of CD8$^+$ T Cell Responses to Newly Identified HLA-A*0201-restricted T Cell Epitopes Conserved Among Vaccinia and Variola (Smallpox) Viruses," *J. Exp. Med.*, 197:927-932, 2003.

Ulmer, J. B., "Heterologous Protection Against Influenza by Injection of DNA Encoding a Viral Protein," *Science*, 259:1745-1749, 1993.

Von Knebel, M. et al., "Correlation of Modified Human Papilloma Virus Early Gene Expression with Altered Growth Properties in C4-1 Cervical Carcinoma Cells," *Cancer Research*, 48:3780-3786, 1988.

Vitiello, A. et al., "Development of a Lipopeptide-based Therapeutic Vaccine to Treat Chronic HBV Infection," *J. Clinical Invest.*, 341-349, 1995.

Wertheimer, A. M. et al., "Novel CD4$^+$ and CD8$^+$ T-Cell Determinants Within the NS3 Protein in Subjects With Spontaneously Resolved HCV Infection," *Hepatology*, 37(3):577-589, 2003.

Wolff, J. A. et al., "Direct Gene Transfer Into Mouse Muscle in Vivo," *Science*, 247:1465-1471, 1990.

Wu, D. Y. et al., "The Ligation Amplification Reaction (LAR)—Amplification of Specific DNA Sequences Using Sequential Rounds of Template-Dependent Ligation," *Genomics*, 4:560-569, 1989.

Zwaveling, S. et al., "Established Human Papillomavirus Type 16-Expressing Tumors Are Effectively Eradicated Following Vaccination with Long Peptides," *The Journal of Immunology*, 169:350-358, 2002.

Karlin, S. et al., "Applications and statistics for multiple high-scoring segments in molecular sequences," *Proc. Natl. Acad. Sci. USA*, 90(12):5873-5877 (1993).

Liu et al., "Sites Internal to the Coding Regions of phoA and pstS Bind PhoP and are Required for Full Promoter Activity," *Molecular Microbiology*, 28(1):119-130 (1998).

Moeller, G. ed., "Antigenic Requirements for Activation of MHC-Restricted Responses," *Immunological Review*, 98:187, Copenhagen, Munksgaard (1987).

Qi et al., "PhoP~P and RNA Polymerase $\sigma^A$ Holoenzyme are Sufficient for Transcription of Pho Regulon Promoters in *Bacillus Subtilis*: PhoP~P Activator Sites Within the Coding Region Stimulate Transcription In Vitro," Molecular Microbiology, 28(6):1187-1197 (1998).

**Singleton et al., *Dictionary of Microbiology and Molecular Biology*, 2nd ed., John Wiley & Sons, New York (1994).

* cited by examiner

SEQUENCE LISTING

```
<160> NUMBER OF SEQ ID NOS: 25

<210> SEQ ID NO 1
<211> LENGTH: 9
<212> TYPE: PRT
<213> ORGANISM: human papillomavirus

<400> SEQUENCE: 1

Met His Gly Asp Thr Pro Thr Leu His
1               5

<210> SEQ ID NO 2
<211> LENGTH: 9
<212> TYPE: PRT
<213> ORGANISM: human papillomavirus

<400> SEQUENCE: 2

Asp Thr Pro Thr Leu His Glu Tyr Met
1               5

<210> SEQ ID NO 3
<211> LENGTH: 9
<212> TYPE: PRT
<213> ORGANISM: human papillomavirus

<400> SEQUENCE: 3

Thr Pro Thr Leu His Glu Tyr Met Leu
1               5

<210> SEQ ID NO 4
<211> LENGTH: 9
<212> TYPE: PRT
```

<213> ORGANISM: human papillomavirus

<400> SEQUENCE: 4

Thr Leu His Glu Tyr Met Leu Asp Leu
1               5

<210> SEQ ID NO 5
<211> LENGTH: 9
<212> TYPE: PRT
<213> ORGANISM: human papillomavirus

<400> SEQUENCE: 5

Leu His Glu Tyr Met Leu Asp Leu Gln
1               5

<210> SEQ ID NO 6
<211> LENGTH: 9
<212> TYPE: PRT
<213> ORGANISM: human papillomavirus

<400> SEQUENCE: 6

His Glu Tyr Met Leu Asp Leu Gln Pro
1               5

<210> SEQ ID NO 7
<211> LENGTH: 9
<212> TYPE: PRT
<213> ORGANISM: human papillomavirus

<400> SEQUENCE: 7

Met Leu Asp Leu Gln Pro Glu Thr Thr
1               5

<210> SEQ ID NO 8
<211> LENGTH: 9
<212> TYPE: PRT
<213> ORGANISM: human papillomavirus

<400> SEQUENCE: 8

Asp Leu Tyr Cys Tyr Glu Gln Leu Asn
1               5

<210> SEQ ID NO 9
<211> LENGTH: 9
<212> TYPE: PRT
<213> ORGANISM: human papillomavirus

<400> SEQUENCE: 9

Asp Glu Ile Asp Gly Pro Ala Gly Gln
1               5

<210> SEQ ID NO 10
<211> LENGTH: 9
<212> TYPE: PRT
<213> ORGANISM: human papillomavirus

<400> SEQUENCE: 10

Gly Gln Ala Glu Pro Asp Arg Ala His
1               5

<210> SEQ ID NO 11
<211> LENGTH: 9
<212> TYPE: PRT
<213> ORGANISM: human papillomavirus

```
<400> SEQUENCE: 11

Ile Val Thr Phe Cys Cys Lys Cys Asp
1               5

<210> SEQ ID NO 12
<211> LENGTH: 9
<212> TYPE: PRT
<213> ORGANISM: human papillomavirus

<400> SEQUENCE: 12

Ile Arg Thr Leu Glu Asp Leu Leu Met
1               5

<210> SEQ ID NO 13
<211> LENGTH: 9
<212> TYPE: PRT
<213> ORGANISM: human papillomavirus

<400> SEQUENCE: 13

Leu Glu Asp Leu Leu Met Gly Thr Leu
1               5

<210> SEQ ID NO 14
<211> LENGTH: 9
<212> TYPE: PRT
<213> ORGANISM: human papillomavirus

<400> SEQUENCE: 14

Glu Asp Leu Leu Met Gly Thr Leu Gly
1               5

<210> SEQ ID NO 15
<211> LENGTH: 9
<212> TYPE: PRT
<213> ORGANISM: human papillomavirus

<400> SEQUENCE: 15

Asp Leu Leu Met Gly Thr Leu Gly Ile
1               5

<210> SEQ ID NO 16
<211> LENGTH: 9
<212> TYPE: PRT
<213> ORGANISM: human papillomavirus

<400> SEQUENCE: 16

Leu Leu Met Gly Thr Leu Gly Ile Val
1               5

<210> SEQ ID NO 17
<211> LENGTH: 9
<212> TYPE: PRT
<213> ORGANISM: human papillomavirus

<400> SEQUENCE: 17

Leu Met Gly Thr Leu Gly Ile Val Cys
1               5

<210> SEQ ID NO 18
<211> LENGTH: 9
<212> TYPE: PRT
<213> ORGANISM: human papillomavirus

<400> SEQUENCE: 18
```

```
Met Gly Thr Leu Gly Ile Val Cys Pro
1               5

<210> SEQ ID NO 19
<211> LENGTH: 9
<212> TYPE: PRT
<213> ORGANISM: human papillomavirus

<400> SEQUENCE: 19

Ile Val Cys Pro Ile Cys Ser Gln Lys
1               5

<210> SEQ ID NO 20
<211> LENGTH: 9
<212> TYPE: PRT
<213> ORGANISM: human papillomavirus

<400> SEQUENCE: 20

Val Leu His Leu Glu Pro Gln Asn Glu
1               5

<210> SEQ ID NO 21
<211> LENGTH: 9
<212> TYPE: PRT
<213> ORGANISM: human papillomavirus

<400> SEQUENCE: 21

Pro Gln Asn Glu Ile Pro Val Asp Leu
1               5

<210> SEQ ID NO 22
<211> LENGTH: 9
<212> TYPE: PRT
<213> ORGANISM: human papillomavirus

<400> SEQUENCE: 22

Ala Arg Arg Ala Glu Pro Gln Arg His
1               5

<210> SEQ ID NO 23
<211> LENGTH: 9
<212> TYPE: PRT
<213> ORGANISM: human papillomavirus

<400> SEQUENCE: 23

Cys Lys Cys Glu Ala Arg Ile Lys Leu
1               5

<210> SEQ ID NO 24
<211> LENGTH: 9
<212> TYPE: PRT
<213> ORGANISM: human papillomavirus

<400> SEQUENCE: 24

Arg Ile Lys Leu Val Val Glu Ser Ser
1               5

<210> SEQ ID NO 25
<211> LENGTH: 9
<212> TYPE: PRT
<213> ORGANISM: human papillomavirus

<400> SEQUENCE: 25
```

```
Ser Phe Val Cys Pro Trp Cys Ala Ser
 1               5
```

HPV CD8+ T-CELL EPITOPES

The present application claims priority to U.S. Provisional Patent Application Ser. No. 60/500,452, filed Sep. 5, 2003.

FIELD OF THE INVENTION

The present invention provides means to identify functional CD8+ T-cell epitopes in any protein of interest. The present invention further provides CD8+ T-cell epitopes of various proteins. In some preferred embodiments, the present invention provides CD8+ T-cell epitopes of human papillomavirus (HPV). In additional embodiments, the present invention provides epitopes suitable for use in prophylactic and/or therapeutic vaccines. In particularly preferred embodiments, the present invention provides modified epitopes suitable for use in prophylactic and/or therapeutic vaccines.

BACKGROUND OF THE INVENTION

Lymphocytes, in particular "B-cells" and "T-cells" are two of the major cell types involved in the immune response of humans and other animals. While B-cells are involved in the humoral aspects of the immune response and are responsible for antibody production, T-cells are involved in the cell mediated aspects of the immune response. However, these two lymphocyte classes work together via a complicated network of recognition factors, cytokines and other elements of the immune response.

Within the T-cells, there are two major cell classes, namely cytotoxic T-cells (Tc) and helper T-cells (Th). Upon activation, cytotoxic T-cells kill infected cells, while helper T-cells activate other cells, such as B-cells and macrophages. Naïve T-cells are activated to produce "armed" effector T-cells upon exposure to a specific antigen that is presented on the surface of an antigen-presenting cell (APC) in conjunction with a component of the major histocompatibility complex (MHC). The two major T-cell classes are often described based on their cell surface receptors. Tc cells are often referred to as "CD8" ("CD8$^+$") cells, and Th cells are often referred to as "CD4" ("CD4$^+$") cells. Despite their different functions, CD4+ and CD8+ cells do not work independently of each other. Indeed, it is known that CD8+ cells are often dependent upon CD4+ cells in mounting a response to an immunogen. Thus, CD8+ cells often require the activation of CD4+ cells in killing infected cells. In addition, it appears that in some cases, CD8+ cells are effective in killing infected cells, while in other cases, these cells are ineffective. However, despite recent advances in the understanding of the immune response, means are still needed for the reliable identification of CD8+ cell epitopes that are effective, as well as means to differentiate effective epitopes from ineffective ones.

SUMMARY OF THE INVENTION

The present invention provides means to identify functional CD8+ T-cell epitopes in any protein of interest. The present invention further provides CD8+ T-cell epitopes of various proteins. In some preferred embodiments, the present invention provides CD8+ T-cell epitopes of human papillomavirus (HPV). The present invention further provides epitopes suitable for use in prophylactic and/or therapeutic vaccines. In particularly preferred embodiments, the present invention provides modified epitopes suitable for use in prophylactic and/or therapeutic vaccines.

The present invention provides means to assay the responses of CD8+ T-cells in a functional manner. In particular, the present invention provides in vitro means to assess CD8+ T-cell responses in the presence of an antibody that mimics T-cell activation in vivo. In some preferred embodiments, the present invention provides means for identifying the immunogenicity of a protein of interest, comprising the steps of: obtaining a protein of interest; preparing a plurality of amino acid fragments of the protein of interest, such that each fragment overlaps in sequence with its contiguous fragments; contacting the amino acid fragments of the protein of interest with a solution comprising naïve human CD8+ T-cells and dendritic cells, wherein the dendritic cells have been differentiated and wherein the CD8+ T-cells have been exposed to anti-CD40 antibody prior to contacting the cells with the dendritic cells and peptides; and identifying an epitope region with the amino acid fragments of the protein of interest, wherein the identifying step comprises measuring the ability of the epitope region to stimulate proliferation of the naïve human CD8+ T-cells. In some particularly preferred embodiments, the dendritic cells and the CD8+ cells are obtained from a single blood source. In additional particularly preferred embodiments, the anti-CD40 antibody is added to the solution after the CD8+ T-cells, dendritic cells and peptides have been combined.

The present invention further provides methods for modifying the immunogenicity of a protein of interest comprising the steps of: obtaining a protein of interest; preparing a plurality of amino acid fragments of the protein of interest, such that each fragment overlaps in sequence with its contiguous fragments; contacting the amino acid fragments of the protein of interest with a solution comprising naïve human CD8+ T-cells and dendritic cells, wherein the dendritic cells have been differentiated and wherein the CD8+ T-cells have been exposed to anti-CD40 antibody either prior to or after contacting the cells with the dendritic cells and peptides; identifying an epitope region with the amino acid fragments of the protein of interest, wherein the identifying step comprises measuring the ability of the epitope region to stimulate proliferation of the naïve human CD8+ T-cells; and then modifying the identified epitope region of the protein of interest, such that the immunogenicity of the modified epitope is either greater or lower than the immunogenicity of the original protein of interest. In some embodiments, multiple epitopes are modified. In some particularly preferred embodiments, the dendritic cells and the CD8+ cells are obtained from a single blood source. In additional particularly preferred embodiments, the anti-CD40 antibody is added to the solution after the CD8+ T-cells, dendritic cells and peptides have been combined.

In some embodiments, the present invention provides methods and compositions for the identification of epitopes in viruses, including but not limited to HPV. In particular, the present invention provides applications for a modified T-cell assay system (i.e., the I-MUNE® assay), for the identification of CD8+ T-cell epitopes in various viruses, including HPV. In additional embodiments, the present invention provides methods for the identification of HPV epitopes in the sequences of various HPV types, as well as the production of peptides which, when incorporated into an HPV sequence, are capable of initiating a CD8+ T-cell response.

In some embodiments, the present invention provides methods for the identification of CD8$^+$ T-cell epitopes in HPV sequences and the production of peptides that are capable of initiating the CD8$^+$ T-cell response. In particular, the present invention provides means and compositions suitable for increasing the immunogenicity of HPV epitopes for use in HPV vaccine preparations.

In these embodiments, the present invention provides means for determining the T-cell responses of humans against various epitopes comprising a protein of interest. In additional embodiments, once the significant epitopes are identified using the I-MUNE® assay system described herein, the significant epitopes are altered to produce epitopes that induce an enhanced immune response to the protein.

Thus, as indicated above, the proteins of the present invention exhibit modified immunogenic responses (e.g., antigenicity and/or immunogenicity) when compared to the native proteins encoded by their precursor DNAs. For example, HPVs that exhibit increased immunogenic responses (e.g. variant HPV epitopes) find use in therapeutic and prophylactic vaccine compositions.

The present invention also provides CD8+ T-cell epitopes in E7 proteins from two strains of human papillomavirus (HPV). In some preferred embodiments, the present invention provides means for the development of HPV vaccines, in particular multivalent vaccines for the prevention of infection with high-risk HPV strains. In additional embodiments, the present invention provides means for the development of therapeutic vaccines against high-risk HPV types suitable for use in the prevention of the development of benign and/or malignant tumors in infected individuals. The present invention further provides epitopes suitable for use in prophylactic and/or therapeutic vaccines. In some preferred embodiments, the present invention provides the epitopes set forth in SEQ ID NOS:1–25. In particularly preferred embodiments, the present invention provides modified epitopes suitable for use in prophylactic and/or therapeutic vaccines.

The present invention further provides compositions and methods for the development of vaccine compositions directed against the E7 proteins of two of the high risk HPV strains (i.e., strains 16 and 18). In some particularly preferred embodiments, the vaccine compositions are comprised of at least one epitope selected from the group selected from SEQ. ID NOS:1 through 25. In some alternatively preferred embodiments, the vaccine compositions comprise epitopes selected from at least one of the high-risk HPV strains and/or at least one of the moderate-risk HPV strains known in the art. Indeed, it is contemplated that the HPV vaccines of the present invention will find use in the treatment and prophylaxis of numerous HPV strains. It is not intended that the present invention be limited to any particular epitopes and/or vaccine compositions comprising any particular epitopes. Thus, in the various vaccine embodiments of the present invention, any combination of epitopes suitable for the intended use find use in the present invention.

DESCRIPTION OF THE FIGURES

FIG. 1 provides a graph showing responses to each epitope in HPV E7.16 tested.

FIG. 2 provides a graph showing responses to each epitope in HPV E7.18 tested.

FIG. 3 provides a graph showing responses to HPV E7.18 in the presence of anti-CD40 antibody and anti-IgG 1 isotype antibody.

FIG. 4 provides a graph showing the responses of twenty random donors that were tested in parallel in an ELISPOT INF-γ assay and the CD8 I-MUNE® assay using HPV18.E7 peptides.

DESCRIPTION OF THE INVENTION

The present invention provides means to identify functional CD8+ T-cell epitopes in any protein of interest. The present invention further provides CD8+ T-cell epitopes of various proteins. In some preferred embodiments, the present invention provides CD8+ T-cell epitopes of human papillomavirus (HPV). In additional embodiments, the present invention provides epitopes suitable for use in prophylactic and/or therapeutic vaccines. In particularly preferred embodiments, the present invention provides modified epitopes suitable for use in prophylactic and/or therapeutic vaccines. In some particularly preferred embodiments, the present invention provides means to develop vaccines based on T-cell epitopes from various strains of microorganisms, including viruses, as well as for prevention of cancer.

As described herein and in U.S. patent application Ser. No. 09/060,872, filed Apr. 15, 1998; Ser. No. 09/500,135, filed Feb. 2, 2000; Ser. No. 09/768,080, filed Jan. 23, 2001; and related applications, the I-MUNE® assay was developed to identify functional T-cell epitopes in any protein of interest. One feature of this assay involves the use of cells obtained from community donors, which is likely to include individuals who have not been exposed to the protein of interest. As described in the cited applications and publications, the assay was used with great success in the identification of CD4+ T-cell epitopes in various proteins. However, results were typically less robust when CD8+ T-cell epitopes were under study. According to the literature, CD8+ T-cell responses are often dependent on CD4+ T-cells to "help" them respond. In part, this help involves the activation of antigen-presenting cells (APCs). APC activation occurs when a CD4+ T-cell interacts with APCs. The interaction between CD4+ T-cells and APC is mediated in part by a CD40 Ligand/CD40 receptor interaction. Thus, during the development of the present invention, anti-CD40 monoclonal antibody was used in the assay as a substitute for the presence of activating CD4+ T-cells.

In addition, it is believed that in some cases, patients who clear diseases have immune responses that are directed against different epitopes than patients who develop chronic disease. Indeed, this has been shown in HCV infected individuals who spontaneously clear the infection (See, Wertheimer et al., Hepatol., 37:577–589 [2003]), and in HIV infected individuals who have robust CD8+ responses while carrying high viral loads (See, Addo et al., J. Virol., 77:2081–2092 [2003]). Thus, the identification of epitopes in normal healthy donors as described herein, will find use in the identification of potentially effective versus non-effective CD8+ epitopes.

As described herein, an anti-CD40 monoclonal antibody was tested in replicates of the CD8+ I-MUNE® assay to assess its effects on the proliferative responses of CD8+ T-cells. As described in greater detail in the Examples, a narrow range of concentrations (in vitro) were found to be effective. As indicated, both CD8+ proliferation, and IFN-γ secretion, were upregulated in vitro by the use of the anti-CD40 antibody. However, as also described herein, a number of other antibodies were tried in similar experiments, but they did not induce CD8+ T-cell activation.

Other methods of functional CD8+ T-cell epitope identification rely on cells from donors carrying memory immune responses. In these assays, peripheral blood mononuclear cells (PBMCs) are used, or are cultured in vitro prior to use, or are cloned. Indeed, most current HPV and other Major Histocompatibility Complex (MHC) Class I epitope peptide identification methods rely on the use of peripheral blood sources from verified exposed donors, who have an enrichment for antigen-specific CD8+ T-cells. For these enriched populations, tetramer staining and proliferative methods can be used. Indeed, tetramer analysis using sets of peptides has been used to find epitope responses in conjunction with Elispot analyses to insure that the CD8 T-cells are functional (See e.g., Terajima et al., J. Exp. Med., 197:927–932 [2003]). However, the use of tetramers is somewhat limited, in that only a handful of Class I constructs are currently available (See e.g., Sato et al., J. Immunol. Meth., 271: 177–184 [2002]; and Altman et al., Science 274:94–96 [1996], erratum at Science 280:1821 [1998]).

In addition, a number of predictive algorithms for CD8+ T-cell epitopes are known, some of which appear to be quite efficient and accurate (See, Nussbaum et al., Curr. Opin. Immunol., 15:69–74 [2003]). In some embodiments, these computer algorithm methods are used to predict MHC Class I binding. However, the entire answer is not provided by these methods as predicted epitopes that are identified based on computer algorithms must also be functionally validated.

The present invention provides significant advantages over the methods currently utilized, as the assay utilizes non-exposed cell donors and does not rely on computer algorithms to assess relationships between epitopes and the immune response. Importantly, the present invention provides means to functionally validate the results obtained for each epitope and sample.

Definitions

Unless defined otherwise herein, all technical and scientific terms used herein have the same meaning as commonly understood by one of ordinary skill in the art to which this invention pertains. For example, Singleton and Sainsbury, *Dictionary of Microbiology and Molecular Biology*, 2d Ed., John Wiley and Sons, NY (1994); and Hale and Marham, *The Harper Collins Dictionary of Biology*, Harper Perennial, N.Y. (1991) provide those of skill in the art with a general dictionaries of many of the terms used in the invention. Although any methods and materials similar or equivalent to those described herein find use in the practice of the present invention, the preferred methods and materials are described herein. Accordingly, the terms defined immediately below are more fully described by reference to the Specification as a whole. Also, as used herein, the singular "a", "an" and "the" includes the plural reference unless the context clearly indicates otherwise. To facilitate understanding of the invention, a number of terms are defined below.

As used herein, "HPV" and "human papillomavirus" refer to the members of the genus *Papillomavirus* that are capable of infecting humans. There are two major groups of HPVs (i.e., genital and cutaneous groups), each of which contains multiple virus "types" or "strains" (e.g., HPV 16, HPV 18, HPV 31, HPV 32, etc.). Of particular interest in the present invention are the HPV types that are associated with genital infection and malignancy.

As used herein, "prophylactic" and "preventive" vaccines are vaccines that are designed and administered to prevent infection, disease, and/or any related sequela(e) caused by or associated with a pathogenic organism, particularly HPV.

As used herein, "therapeutic" vaccines are vaccines that are designed and administered to patients already infected with a pathogenic organism such as at least one HPV strain. Therapeutic vaccines (e.g., therapeutic HPV vaccines) are used to prevent and/or treat the development of benign or malignant tumors in these infected individuals.

"Antigen presenting cells" ("APC") as used herein refers to cells of the immune system which present antigen on their surfaces. This antigen is recognizable by T-cells. Examples of antigen presenting cells are dendritic cells, interdigitating cells, activated B-cells and macrophages.

The term "lymphoid" when used in reference to a cell line or a cell, means that the cell line or cell is derived from the lymphoid lineage and includes cells of both the B and the T lymphocyte lineages.

As used herein, the terms "T lymphocyte" and "T-cell," encompass any cell within the T lymphocyte lineage from T-cell precursors (including Thy1 positive cells which do not have rearranged T-cell receptor [TCR] genes) to mature T-cells (i.e., single positive for either CD4+ or CD8+, surface TCR positive cells).

As used herein, the terms "B lymphocyte" and "B-cell" encompasses any cell within the B-cell lineage from B-cell precursors, such as pre-B-cells (B220+cells which have begun to rearrange Ig heavy chain genes), to mature B-cells and plasma cells.

As used herein, "CD4$^+$ T-cell" and "CD4 T-cell" refer to helper T-cells, while "CD8$^+$ T-cell" and "CD8 T-cell" refer to cytotoxic T-cells.

As used herein, "B-cell proliferation," refers to the increased number of B-cells produced during the incubation of B-cells with the antigen presenting cells, with or without antigen.

As used herein, "baseline B-cell proliferation," as used herein, refers to the degree of B-cell proliferation that is normally seen in an individual in response to exposure to antigen presenting cells in the absence of peptide or protein antigen. For the purposes herein, the baseline B-cell proliferation level is determined on a per sample basis for each individual as the proliferation of B-cells in the absence of antigen.

As used herein, "B-cell epitope," refers to a feature of a peptide or protein that is recognized by a B-cell receptor in the immunogenic response to the peptide comprising that antigen (i.e., the immunogen).

As used herein, "altered B-cell epitope," refers to an epitope amino acid sequence which differs from the precursor peptide or peptide of interest, such that the variant peptide of interest produces different (i.e., altered) immunogenic responses in a human or another animal. It is contemplated that an altered immunogenic response includes altered immunogenicity and/or allergenicity (i.e., an either increased or decreased overall immunogenic response). In some embodiments, the altered B-cell epitope comprises substitution and/or deletion of an amino acid selected from those residues within the identified epitope. In alternative embodiments, the altered B-cell epitope comprises an addition of one or more residues within the epitope.

As used herein "T-cell epitope" means a feature of a peptide or protein that is recognized by a T-cell receptor in the initiation of an immunologic response to the peptide comprising that antigen. Recognition of a T-cell epitope by a T-cell is generally believed to be via a mechanism wherein T-cells recognize peptide fragments of antigens which are bound to Class I or Class II Major Histocompatibility Complex (MHC) molecules expressed on antigen-presenting cells (See e.g., Moeller (ed.), Immunol. Rev., 98:187

[1987]). In some embodiments of the present invention, the epitopes or epitopic fragments identified as described herein find use in the detection of antigen presenting cells having MHC molecules capable of binding and displaying the epitopes or fragments. In some embodiments, the epitopes/ epitopic fragments further comprise a detectable label (i.e., a marker) that facilitates the identification of cells that bind and/or display the epitope/epitopic fragment of interest.

As used herein, "T-cell proliferation," refers to the number of T-cells produced during the incubation of T-cells with the antigen presenting cells, with or without antigen. "Baseline T-cell proliferation," as used herein, refers to the degree of T-cell proliferation that is normally seen in an individual in response to exposure to antigen presenting cells in the absence of peptide or protein antigen. For the purposes herein, the baseline T-cell proliferation level is determined on a per sample basis for each individual as the proliferation of T-cells in response to antigen presenting cells in the absence of antigen.

As used herein "altered immunogenic response," refers to an increased or reduced immunogenic response. Proteins and peptides exhibit an "increased immunogenic response" when the T-cell and/or B-cell response they evoke is greater than that evoked by a parental (e.g., precursor) protein or peptide (e.g., the protein of interest). Typically, the net result of this higher response is an increased antibody response directed against the variant protein or peptide. Proteins and peptides exhibit a "reduced immunogenic response" when the T-cell and/or B-cell response they evoke is less than that evoked by a parental (e.g., precursor) protein or peptide. In some embodiments, the net result of this lower response is a reduced antibody response directed against the variant protein or peptide. In some preferred embodiments, the parental protein is a wild-type protein or peptide.

With regard to a particular amino acid sequence, an "epitope" is a set of amino acid residues which is involved in recognition by a particular immunoglobulin, or in the context of T-cells, those residues necessary for recognition by T-cell receptor proteins and/or Major Histocompatibility Complex (MHC) receptors. In an immune system setting, in vivo or in vitro, an epitope is the collective features of a molecule, such as primary, secondary and tertiary peptide structure, and charge, that together form a site recognized by an immunoglobulin, T-cell receptor or HLA molecule. Throughout this disclosure, "epitope" and "peptide" are often used interchangeably.

As used herein, the term "major epitope" refers to an epitope (i.e., a T-cell and/or B-cell epitope), wherein the response rate within the tested donor pool is at least three standard deviations above the mean background response rate.

As used herein, the term "moderate epitope" refers to an epitope (i.e., a T-cell and/or B-cell epitope), wherein the response rate within the tested donor pool is at least two standard deviations above the mean or three times the background.

As used herein, the term "minor epitope" refers to an epitope (i.e., a T-cell and/or B-cell epitope), wherein the response rate within the tested donor pool is at least twice the background.

As used herein, the term "significant epitope" refers to an epitope (i.e., a T-cell and/or B-cell epitope), wherein the response rate within the tested donor pool is equal to or greater than about three times the background response rate. As used herein, a "weakly significant epitope" refers to an epitope (i.e., a T-cell and/or B-cell epitope), wherein the response rate within the tested donor pool is greater than the background response rate, but less than about three times the background rate.

As used herein, "background level" and "background response" refer to the average percent of responders to any given peptide in the dataset for any tested protein. This value is determined by averaging the percent responders for all peptides in the set, as compiled for all the tested donors. As an example, a 3% background response would indicate that on average there would be three positive (SI greater than 2.95) responses for any peptide in a dataset when tested on 100 donors.

The term "sample" as used herein is used in its broadest sense. However, in preferred embodiments, the term is used in reference to a sample (e.g., an aliquot) that comprises a peptide (i.e., a peptide within a pepset, that comprises a sequence of a protein of interest) that is being analyzed, identified, modified, and/or compared with other peptides. Thus, in most cases, this term is used in reference to material that includes a protein or peptide that is of interest.

As used herein, "protein of interest," refers to a protein which is being analyzed, identified and/or modified. Naturally-occurring, as well as recombinant proteins, synthetically produced, variant and derivative proteins, all find use in the present invention.

As used herein, "protein" refers to any composition comprised of amino acids and recognized as a protein by those of skill in the art. The terms "protein," "peptide" and polypeptide are used interchangeably herein. Amino acids may be referred to by their complete names (e.g., alanine) or by the accepted one letter (e.g., A), or three letter (e.g., ala) abbreviations. Wherein a peptide is a portion of a protein, those skill in the art understand the use of the term in context. The term "protein" encompasses mature forms of proteins, as well as the pro- and prepro-forms of related proteins. Prepro-forms of proteins comprise the mature form of the protein having a prosequence operably linked to the amino terminus of the protein, and a "pre-" or "signal" sequence operably linked to the amino terminus of the prosequence.

As used herein, functionally similar proteins are considered to be "related proteins." In some embodiments, these proteins are derived from a different genus and/or species, including differences between classes of organisms (e.g., a bacterial protein and a fungal protein). In additional embodiments, related proteins are provided from the same species. Indeed, it is not intended that the present invention be limited to related proteins from any particular source(s).

As used herein, the term "derivative" refers to a protein which is derived from a precursor protein by addition of one or more amino acids to either or both the C- and N-terminal end(s), substitution of one or more amino acids at one or a number of different sites in the amino acid sequence, and/or deletion of one or more amino acids at either or both ends of the protein or at one or more sites in the amino acid sequence, and/or insertion of one or more amino acids at one or more sites in the amino acid sequence. The preparation of a protein derivative is preferably achieved by modifying a DNA sequence which encodes for the native protein, transformation of that DNA sequence into a suitable host, and expression of the modified DNA sequence to form the derivative protein.

One type of related (and derivative) proteins are "variant proteins." In preferred embodiments, variant proteins differ from a parent protein and one another by a small number of amino acid residues. The number of differing amino acid residues may be one or more, preferably 1, 2, 3, 4, 5, 10, 15, 20, 30, 40, 50, or more amino acid residues. In one preferred embodiment, the number of different amino acids between variants is between 1 and 10. In particularly preferred embodiments, related proteins and particularly variant proteins comprise at least 50%, 60%, 65%. 70%, 75%, 80%, 85%, 90%, 95%, 97%, 98%, or 99% amino acid sequence identity. Additionally, a related protein or a variant protein as used herein, refers to a protein that differs from another related protein or a parent protein in the number of prominent regions. For example, in some embodiments, variant proteins have 1, 2, 3, 4, 5, or 10 corresponding prominent regions that differ from the parent protein.

In one embodiment, the prominent corresponding region of a variant produces only a background level immunogenic response. Some of the residues identified for substitution, insertion or deletion are conserved residues whereas others are not. In the case of residues which are not conserved, the replacement of one or more amino acids is limited to substitutions which produce a variant which has an amino acid sequence that does not correspond to one found in nature. In the case of conserved residues, such replacements should not result in a naturally-occurring sequence.

In some embodiments, the following cassette mutagenesis method finds use in the construction of the protein variants of the present invention, although other methods may be used. First, the naturally-occurring gene encoding the protein is obtained and sequenced in whole or in part. Then the sequence is scanned for a point at which it is desired to make a mutation (deletion, insertion or substitution) of one or more amino acids in the encoded protein. The sequences flanking this point are evaluated for the presence of restriction sites for replacing a short segment of the gene with an oligonucleotide pool which when expressed will encode various mutants. Such restriction sites are preferably unique sites within the protein gene so as to facilitate the replacement of the gene segment. However, any convenient restriction site which is not overly redundant in the protein gene may be used, provided the gene fragments generated by restriction digestion can be reassembled in proper sequence. If restriction sites are not present at locations within a convenient distance from the selected point (from 10 to 15 nucleotides), such sites are generated by substituting nucleotides in the gene in such a fashion that neither the reading frame nor the amino acids encoded are changed in the final construction. Mutation of the gene in order to change its sequence to conform to the desired sequence is accomplished by M13 primer extension in accord with generally known methods. The task of locating suitable flanking regions and evaluating the needed changes to arrive at two convenient restriction site sequences is made routine by the redundancy of the genetic code, a restriction enzyme map of the gene and the large number of different restriction enzymes. Note that if a convenient flanking restriction site is available, the above method need be used only in connection with the flanking region which does not contain a site.

Once the naturally-occurring DNA or synthetic DNA is cloned, the restriction sites flanking the positions to be mutated are digested with the cognate restriction enzymes and a plurality of end termini-complementary oligonucleotide cassettes are ligated into the gene. The mutagenesis is simplified by this method because all of the oligonucleotides can be synthesized so as to have the same restriction sites, and no synthetic linkers are necessary to create the restriction sites.

As used herein, "corresponding to," refers to a residue at the enumerated position in a protein or peptide, or a residue that is analogous, homologous, or equivalent to an enumerated residue in a protein or peptide.

As used herein, "corresponding region" generally refers to an analogous position along related proteins or a parent protein.

As used herein, the term "analogous sequence" refers to a sequence within a protein that provides similar function, tertiary structure, and/or conserved residues as the protein of interest (i.e., typically the original protein of interest). In particularly preferred embodiments, the analogous sequence involves sequence(s) at or near an epitope. For example, in epitope regions that contain an alpha helix or a beta sheet structure, the replacement amino acids in the analogous sequence preferably maintain the same specific structure. The term also refers to nucleotide sequences, as well as amino acid sequences. In some embodiments, analogous sequences are developed such that the replacement amino acids show a similar function, the tertiary structure and/or conserved residues to the amino acids in the protein of interest at or near the epitope. Thus, where the epitope region contains, for example, an alpha-helix or a beta-sheet structure, the replacement amino acids preferably maintain that specific structure.

As used herein, "homologous protein" refers to a protein that has similar action, structure, antigenic, and/or immunogenic response as the protein of interest. It is not intended that a homolog and a protein of interest be necessarily related evolutionarily. Thus, it is intended that the term encompass the same functional protein obtained from different species. In some preferred embodiments, it is desirable to identify a homolog that has a tertiary and/or primary structure similar to the protein of interest, as replacement for the epitope in the protein of interest with an analogous segment from the homolog will reduce the disruptiveness of the change. Thus, in most cases, closely homologous proteins provide the most desirable sources of epitope substitutions. Alternatively, it is advantageous to look to human analogs for a given protein. For example, in some embodiments, substituting a specific epitope in one human HPV type with a sequence from another HPV or other species' papillomavirus results in the production of an HPV type that increases immunogenicity to a level suitable for use in vaccine preparations.

As used herein, "homologous genes" refers to at least a pair of genes from different, but usually related species, which correspond to each other and which are identical or very similar to each other. The term encompasses genes that are separated by speciation (i.e., the development of new species) (e.g., orthologous genes), as well as genes that have been separated by genetic duplication (e.g., paralogous genes). These genes encode "homologous proteins."

As used herein, "ortholog" and "orthologous genes" refer to genes in different species that have evolved from a common ancestral gene (i.e., a homologous gene) by speciation. Typically, orthologs retain the same function in during the course of evolution. Identification of orthologs finds use in the reliable prediction of gene function in newly sequenced genomes.

As used herein, "paralog" and "paralogous genes" refer to genes that are related by duplication within a genome. While orthologs retain the same function through the course of evolution, paralogs evolve new functions, even though some functions are often related to the original one. Examples of paralogous genes include, but are not limited to genes encoding trypsin, chymotrypsin, elastase, and thrombin, which are all serine proteinases and occur together within the same species.

As used herein, "wild-type" and "native" proteins are those found in nature. The terms "wild-type sequence," and "wild-type gene" are used interchangeably herein, to refer to a sequence that is native or naturally occurring in a host cell. In some embodiments, the wild-type sequence refers to a sequence of interest that is the starting point of a protein engineering project. The genes encoding the naturally-occurring (i.e., precursor) protein may be obtained in accord with the general methods known to those skilled in the art. The methods generally comprise synthesizing labeled probes having putative sequences encoding regions of the protein of interest, preparing genomic libraries from organisms expressing the protein, and screening the libraries for the gene of interest by hybridization to the probes. Positively hybridizing clones are then mapped and sequenced.

The term "recombinant DNA molecule" as used herein refers to a DNA molecule that is comprised of segments of DNA joined together by means of molecular biological techniques.

The degree of homology between sequences may be determined using any suitable method known in the art (See e.g., Smith and Waterman, Adv. Appl. Math., 2:482 [1981]; Needleman and Wunsch, J. Mol. Biol., 48:443 [1970]; Pearson and Lipman, Proc. Natl. Acad. Sci. USA 85:2444 [1988]; programs such as GAP, BESTFIT, FASTA, and TFASTA in the Wisconsin Genetics Software Package (Genetics Computer Group, Madison, Wis.); and Devereux et al., Nucl. Acid Res., 12:387–395 [1984]).

For example, PILEUP is a useful program to determine sequence homology levels. PILEUP creates a multiple sequence alignment from a group of related sequences using progressive, pairwise alignments. It can also plot a tree showing the clustering relationships used to create the alignment. PILEUP uses a simplification of the progressive alignment method of Feng and Doolittle, (Feng and Doolittle, J. Mol. Evol., 35:351–360 [1987]). The method is similar to that described by Higgins and Sharp (Higgins and Sharp, CABIOS 5:151–153 [1989]). Useful PILEUP parameters including a default gap weight of 3.00, a default gap length weight of 0.10, and weighted end gaps. Another example of a useful algorithm is the BLAST algorithm, described by Altschul et al., (Altschul et al., J. Mol. Biol., 215:403–410, [1990]; and Karlin et al., Proc. Natl. Acad. Sci. USA 90:5873–5787 [1993]). One particularly useful BLAST program is the WU-BLAST-2 program (See, Altschul et al., Meth. Enzymol., 266:460–480 [1996]). parameters "W," "T," and "X" determine the sensitivity and speed of the alignment. The BLAST program uses as defaults a wordlength (W) of 11, the BLOSUM62 scoring matrix (See, Henikoff and Henikoff, Proc. Natl. Acad. Sci. USA 89:10915 [1989]) alignments (B) of 50, expectation (E) of 10, M'5, N'-4, and a comparison of both strands.

As used herein, "percent (%) nucleic acid sequence identity" is defined as the percentage of nucleotide residues in a candidate sequence that are identical with the nucleotide residues of the sequence.

As used herein, the term "hybridization" refers to the process by which a strand of nucleic acid joins with a complementary strand through base pairing, as known in the art.

As used herein, "maximum stringency" refers to the level of hybridization that typically occurs at about Tm-5° C. (5° C. below the Tm of the probe); "high stringency" at about 5° C. to 10° C. below Tm; "intermediate stringency" at about 10° C. to 20° C. below Tm; and "low stringency" at about 20° C. to 25° C. below Tm. As will be understood by those of skill in the art, a maximum stringency hybridization can be used to identify or detect identical polynucleotide sequences while an intermediate or low stringency hybridization can be used to identify or detect polynucleotide sequence homologs.

The phrases "substantially similar and "substantially identical" in the context of two nucleic acids or polypeptides typically means that a polynucleotide or polypeptide comprises a sequence that has at least 75% sequence identity, preferably at least 80%, more preferably at least 90%, still more preferably 95%, most preferably 97%, sometimes as much as 98% and 99% sequence identity, compared to the reference (i.e., wild-type) sequence. Sequence identity may be determined using—known programs such as BLAST, ALIGN, and CLUSTAL using standard parameters. (See e.g., Altschul, et al., J. Mol. Biol. 215:403–410 [1990]; Henikoff et al., Proc. Natl. Acad. Sci. USA 89:10915 [1989]; Karin et al., Proc. Natl. Acad. Sci USA 90:5873 [1993]; and Higgins et al., Gene 73:237–244 [1988]). Software for performing BLAST analyses is publicly available through the National Center for Biotechnology Information. Also, databases may be searched using FASTA (Pearson et al., Proc. Natl. Acad. Sci. USA 85:2444–2448 [1988]).

As used herein, "equivalent residues" refers to proteins that share particular amino acid residues. For example, equivalent resides may be identified by determining homology at the level of tertiary structure for a protein (e.g. IFN-β) whose tertiary structure has been determined by x-ray crystallography. Equivalent residues are defined as those for which the atomic coordinates of two or more of the main chain atoms of a particular amino acid residue of the protein having putative equivalent residues and the protein of interest (N on N, CA on CA, C on C and O on O) are within 0.13 nm and preferably 0.1 nm after alignment. Alignment is achieved after the best model has been oriented and positioned to give the maximum overlap of atomic coordinates of non-hydrogen protein atoms of the proteins analyzed. The preferred model is the crystallographic model giving the lowest R factor for experimental diffraction data at the highest resolution available, determined using methods known to those skilled in the art of crystallography and protein characterization/analysis.

In some embodiments, modification is preferably made to the "precursor DNA sequence" which encodes the amino acid sequence of the precursor enzyme, but can be by the manipulation of the precursor protein. In the case of residues which are not conserved, the replacement of one or more amino acids is limited to substitutions which produce a variant which has an amino acid sequence that does not correspond to one found in nature. In the case of conserved residues, such replacements should not result in a naturally-occurring sequence. Derivatives provided by the present invention further include chemical modification(s) that change the characteristics of the protease.

In some preferred embodiments, the protein gene is ligated into an appropriate expression plasmid. The cloned protein gene is then used to transform or transfect a host cell in order to express the protein gene. This plasmid may replicate in hosts in the sense that it contains the well-known elements necessary for plasmid replication or the plasmid may be designed to integrate into the host chromosome. The necessary elements are provided for efficient gene expression (e.g., a promoter operably linked to the gene of interest). In some embodiments, these necessary elements are supplied as the gene's own homologous promoter if it is recognized, (i.e., transcribed, by the host), a transcription terminator (a polyadenylation region for eukaryotic host cells) which is exogenous or is supplied by the endogenous terminator region of the protein gene. In some embodiments, a selection gene such as an antibiotic resistance gene that enables continuous cultural maintenance of plasmid-infected host cells by growth in antimicrobial-containing media is also included.

The present invention encompasses proteins having altered immunogenicity that are equivalent. Being "equivalent," means that the proteins are encoded by a polynucleotide capable of hybridizing to the polynucleotide having the sequence as shown in any one of those provided herein, under conditions of medium to high stringency and still retaining the altered immunogenic response to human T-cells. Being "equivalent" means that the protease comprises at least 55%, at least 65%, at least 70%, at least 75%, at least 80%, at least 85%, at least 90%, at least 95%, at least 97% or at least 99% identity to the epitope sequences and the variant proteases having such epitopes (e.g., having the amino acid sequence modified).

As used herein, the terms "hybrid proteins" and "fusion proteins" refer to proteins that are engineered from at least two different or "parental" proteins. In preferred embodiments, these parental proteins are homologs of one another. For example, in some embodiments, a preferred hybrid protease or fusion protein contains the N-terminus of a protein and the C-terminus of a homolog of the protein. In some preferred embodiment, the two terminal ends are combined to correspond to the full-length active protein. In alternative preferred embodiments, the homologs share substantial similarity but do not have identical T-cell epitopes. Therefore, in one embodiment, the present invention provides a protease of interest having one or more T-cell epitopes in the C-terminus, but in which the C-terminus is replaced with the C-terminus of a homolog having a less potent T-cell epitope, or fewer or no T-cell epitopes in the C-terminus. Thus, the skilled artisan understands that by being able to identify T-cell epitopes among homologs, a variety of variants producing different immunogenic responses can be formed. Moreover, it is understood that internal portions, and more than one homolog can be used to produce the variants of the present invention.

"Operably linked" and "in operable combination," when describing the relationship between two DNA regions, simply means that they are functionally related to each other. For example, a presequence is operably linked to a peptide if it functions as a signal sequence, participating in the secretion of the mature form of the protein most probably involving cleavage of the signal sequence. A promoter is operably linked to a coding sequence if it controls the transcription of the sequence; a ribosome binding site is operably linked to a coding sequence if it is positioned so as to permit translation.

DNA molecules are said to have "5' ends" and "3' ends" because mononucleotides are reacted to make oligonucleotides in a manner such that the 5' phosphate of one mononucleotide pentose ring is attached to the 3' oxygen of its neighbor in one direction via a phosphodiester linkage. Therefore, an end of an oligonucleotides is referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide, also may be said to have 5' and 3' ends. In either a linear or circular DNA molecule, discrete elements are referred to as being "upstream" or 5' of the "downstream" or 3' elements. This terminology reflects the fact that transcription proceeds in a 5' to 3' fashion along the DNA strand. The promoter and enhancer elements which direct transcription of a linked gene are generally located 5' or upstream of the coding region (enhancer elements can exert their effect even when located 3' of the promoter element and the coding region). Transcription termination and polyadenylation signals are located 3' or downstream of the coding region.

The term "an oligonucleotide having a nucleotide sequence encoding a gene" means a DNA sequence comprising the coding region of a gene or, in other words, the DNA sequence that encodes a gene product. The coding region may be present in either a cDNA or genomic DNA form. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc. or a combination of both endogenous and exogenous control elements.

The term "recombinant oligonucleotide" refers to an oligonucleotide created using molecular biological manipulations, including but not limited to, the ligation of two or more oligonucleotide sequences generated by restriction enzyme digestion of a polynucleotide sequence, the synthesis of oligonucleotides (e.g., the synthesis of primers or oligonucleotides) and the like.

The term "transcription unit" as used herein refers to the segment of DNA between the sites of initiation and termination of transcription and the regulatory elements necessary for the efficient initiation and termination. For example, a segment of DNA comprising an enhancer/promoter, a coding region, and a termination and polyadenylation sequence comprises a transcription unit.

The term "regulatory element" as used herein refers to a genetic element that controls some aspect of the expression of nucleic acid sequences. For example, a promoter is a regulatory element which facilitates the initiation of transcription of an operably linked coding region. Other regulatory elements are splicing signals, polyadenylation signals, termination signals, etc. (defined infra).

The term "expression vector" as used herein refers to a recombinant DNA molecule containing a desired coding sequence and appropriate nucleic acid sequences necessary for the expression of the operably linked coding sequence in a particular host organism. Nucleic acid sequences necessary for expression in prokaryotes include a promoter, optionally an operator sequence, a ribosome binding site and possibly other sequences. Eukaryotic cells are known to utilize promoters, enhancers, and termination and polyadenylation signals. Once transformed into a suitable host, the vector may replicate and function independently of the host genome, or may, in some instances, integrate into the genome itself. In the present specification, "plasmid" and "vector" are sometimes used interchangeably as the plasmid is the most commonly used form of vector at present. However, the invention is intended to include such other forms of expression vectors which serve equivalent functions and which are, or become, known in the art, including but not limited to plasmids, phage particles, viral vectors, and/or simply potential genomic inserts.

The "host cells" used in the present invention generally are prokaryotic or eukaryotic hosts which contain an expression vector and/or gene of interest. Host cells are transformed or transfected with vectors constructed using recombinant DNA techniques. Such transformed host cells are capable of either replicating vectors encoding the protein variants or expressing the desired protein variant. In the case of vectors which encode the pre- or prepro-form of the protein variant, such variants, when expressed, are typically secreted from the host cell into the host cell medium.

The term "promoter/enhancer" denotes a segment of DNA which contains sequences capable of providing both promoter and enhancer functions (for example, the long terminal repeats of retroviruses contain both promoter and enhancer functions). The enhancer/promoter may be "endogenous" or "exogenous" or "heterologous." An endogenous enhancer/promoter is one which is naturally linked with a given gene in the genome. An exogenous (heterologous) enhancer/promoter is one which is placed in juxtaposition to a gene by means of genetic manipulation (i.e., molecular biological techniques).

The presence of "splicing signals" on an expression vector often results in higher levels of expression of the recombinant transcript. Splicing signals mediate the removal of introns from the primary RNA transcript and consist of a splice donor and acceptor site (Sambrook et al., Molecular Cloning: A Laboratory Manual, 2nd ed., Cold Spring Harbor Laboratory Press, New York [1989], pp. 16.7–16.8). A commonly used splice donor and acceptor site is the splice junction from the 16S RNA of SV40.

Efficient expression of recombinant DNA sequences in eukaryotic cells requires signals directing the efficient termination and polyadenylation of the resulting transcript. Transcription termination signals are generally found downstream of the polyadenylation signal and are a few hundred nucleotides in length. The term "poly A site" or "poly A sequence" as used herein denotes a DNA sequence which directs both the termination and polyadenylation of the nascent RNA transcript. Efficient polyadenylation of the recombinant transcript is desirable as transcripts lacking a poly A tail are unstable and are rapidly degraded. The poly A signal utilized in an expression vector may be "heterologous" or "endogenous." An endogenous poly A signal is one that is found naturally at the 3' end of the coding region of a given gene in the genome. A heterologous poly A signal is one which is isolated from one gene and placed 3' of another gene. A commonly used heterologous poly A signal is the SV40 poly A signal.

The terms "stable transfection" and "stably transfected" refer to the introduction and integration of foreign DNA into the genome of the transfected cell. The term "stable transfectant" refers to a cell which has stably integrated foreign DNA into the genomic DNA.

The terms "selectable marker" and "selectable gene product" as used herein refer to the use of a gene which encodes an enzymatic activity that confers resistance to an antibiotic or drug upon the cell in which the selectable marker is expressed.

As used herein, the terms "amplification" and "gene amplification" refer to a process by which specific DNA sequences are disproportionately replicated such that the amplified gene becomes present in a higher copy number than was initially present in the genome. In some embodiments, selection of cells by growth in the presence of a drug (e.g., an inhibitor of an inhibitable enzyme) results in the amplification of either the endogenous gene encoding the gene product required for growth in the presence of the drug or by amplification of exogenous (i.e., input) sequences encoding this gene product, or both. Gene amplification occurs naturally during development in particular genes such as the amplification of ribosomal genes in amphibian oocytes. Gene amplification may be induced by treating cultured cells with drugs. An example of drug-induced amplification is the methotrexate-induced amplification of the endogenous dhfr gene in mammalian cells (Schmike et al., Science 202:1051 [1978]). Selection of cells by growth in the presence of a drug (e.g., an inhibitor of an inhibitable enzyme) may result in the amplification of either the endogenous gene encoding the gene product required for growth in the presence of the drug or by amplification of exogenous (i.e., input) sequences encoding this gene product, or both.

Amplification is a special case of nucleic acid replication involving template specificity. It is to be contrasted with non-specific template replication (i.e., replication that is template-dependent but not dependent on a specific template). Template specificity is here distinguished from fidelity of replication (i.e., synthesis of the proper polynucleotide sequence) and nucleotide (ribo- or deoxyribo-) specificity. Template specificity is frequently described in terms of "target" specificity. Target sequences are "targets" in the sense that they are sought to be sorted out from other nucleic acid. Amplification techniques have been designed primarily for this sorting out.

As used herein, the term "co-amplification" refers to the introduction into a single cell of an amplifiable marker in conjunction with other gene sequences (i.e., comprising one or more non-selectable genes such as those contained within an expression vector) and the application of appropriate selective pressure such that the cell amplifies both the amplifiable marker and the other, non-selectable gene sequences. The amplifiable marker may be physically linked to the other gene sequences or alternatively two separate pieces of DNA, one containing the amplifiable marker and the other containing the non-selectable marker, may be introduced into the same cell.

As used herein, the terms "amplifiable marker," "amplifiable gene," and "amplification vector" refer to a gene or a vector encoding a gene which permits the amplification of that gene under appropriate growth conditions.

As used herein, the term "amplifiable nucleic acid" refers to nucleic acids which may be amplified by any amplification method. It is contemplated that "amplifiable nucleic acid" will usually comprise "sample template."

As used herein, the term "sample template" refers to nucleic acid originating from a sample which is analyzed for the presence of "target" (defined below). In contrast, "background template" is used in reference to nucleic acid other than sample template which may or may not be present in a sample. Background template is most often inadvertent. It may be the result of carryover, or it may be due to the presence of nucleic acid contaminants sought to be purified away from the sample. For example, nucleic acids from organisms other than those to be detected may be present as background in a test sample.

"Template specificity" is achieved in most amplification techniques by the choice of enzyme. Amplification enzymes are enzymes that, under conditions they are used, will process only specific sequences of nucleic acid in a heterogeneous mixture of nucleic acid. For example, in the case of Qβ replicase, MDV-1 RNA is the specific template for the replicase (See e.g., Kacian et al., Proc. Natl. Acad. Sci. USA 69:3038 [1972]). Other nucleic acids are not replicated by this amplification enzyme. Similarly, in the case of T7 RNA polymerase, this amplification enzyme has a stringent specificity for its own promoters (See, Chamberlin et al., Nature 228:227 [1970]). In the case of T4 DNA ligase, the enzyme will not ligate the two oligonucleotides or polynucleotides, where there is a mismatch between the oligonucleotide or polynucleotide substrate and the template at the ligation junction (See, Wu and Wallace, Genomics 4:560 [1989]). Finally, Taq and Pfu polymerases, by virtue of their ability to function at high temperature, are found to display high specificity for the sequences bounded and thus defined by the primers; the high temperature results in thermodynamic conditions that favor primer hybridization with the target sequences and not hybridization with non-target sequences.

As used herein, the term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

As used herein, the term "probe" refers to an oligonucleotide (i.e., a sequence of nucleotides), whether occurring naturally as in a purified restriction digest or produced synthetically, recombinantly or by PCR amplification, which is capable of hybridizing to another oligonucleotide of interest. A probe may be single-stranded or double-stranded.

Probes are useful in the detection, identification and isolation of particular gene sequences. It is contemplated that any probe used in the present invention will be labeled with any "reporter molecule," so that is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

As used herein, the term "target," when used in reference to the polymerase chain reaction, refers to the region of nucleic acid bounded by the primers used for polymerase chain reaction. Thus, the "target" is sought to be sorted out from other nucleic acid sequences. A "segment" is defined as a region of nucleic acid within the target sequence.

As used herein, the term "polymerase chain reaction" ("PCR") refers to the methods of U.S. Pat. Nos. 4,683,195 4,683,202, and 4,965,188, hereby incorporated by reference, which include methods for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified".

As used herein, the term "amplification reagents" refers to those reagents (deoxyribonucleotide triphosphates, buffer, etc.), needed for amplification except for primers, nucleic acid template and the amplification enzyme. Typically, amplification reagents along with other reaction components are placed and contained in a reaction vessel (test tube, microwell, etc.).

With PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection; incorporation of $^{32}$P-labeled deoxynucleotide triphosphates, such as dCTP or dATP, into the amplified segment). In addition to genomic DNA, any oligonucleotide or polynucleotide sequence can be amplified with the appropriate set of primer molecules. In particular, the amplified segments created by the PCR process itself are, themselves, efficient templates for subsequent PCR amplifications.

As used herein, the terms "PCR product," "PCR fragment," and "amplification product" refer to the resultant mixture of compounds after two or more cycles of the PCR steps of denaturation, annealing and extension are complete. These terms encompass the case where there has been amplification of one or more segments of one or more target sequences.

As used herein, the terms "restriction endonucleases" and "restriction enzymes" refer to bacterial enzymes, each of which cut double-stranded DNA at or near a specific nucleotide sequence.

The terms "nucleic acid molecule encoding," "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

The peptides of the present invention and pharmaceutical and vaccine compositions thereof are useful for administration to mammals, particularly humans, to treat and/or prevent HPV infection. Vaccines that contain an immunogenically effective amount of one or more peptides as described herein are a further embodiment of the invention. Once appropriately immunogenic epitopes have been defined, they can be delivered by various means, herein referred to as "vaccine" compositions. Such vaccine compositions can include, for example, lipopeptides (e.g., Vitiello et al., J. Clin. Invest., 95:341 [1995]; and PCTUSOO/17842; peptide compositions encapsulated in poly(DL-lactide-co-glycolide) ("TLG") microspheres (See e.g., Eldridge et al., Molec. Immunol., 28:287–294 [1991]: Alonso et al., Vaccine 12:299–306 [1994]; Jones et al., Vaccine 13:675–681 [1995]), peptide compositions contained in immune stimulating complexes (ISCOMS) (See e.g., Takahashi et al., Nature 344:873–875 [1990]; Hu et al., Clin. Exp. Immunol., 113:235–243 [1998]), multiple antigen peptide systems (MAPs) (See e.g., Tam, Proc. Natl. Acad. Sci. U.S.A. 85:5409–5413 [1988]; Tam, J. Immunol. Meth., 196:17–32 [1996]), viral delivery vectors (Perkus et al., In: *Concepts in Vaccine Development*, Kaufmann (ed.), p. 379 [1996]; Chakrabarti et al., Nature 320:535 [1986]; Hu et al., Nature 320:537 [1986]; Kieny et al., AIDS Bio/Technol., 4:790 [1986]; Top et al., J. Infect. Dis., 124:148 [1971]; Chanda et al., Virol., 175:535 [1990]), particles of viral or synthetic origin (e.g., Kofler et al., J. Immunol., Meth., 192:25 [1996]; Eldridge et al., Sem. Hematol., 30:16 [1993]; Falo et al., Nature Med., 7:649 [1995]), adjuvants (Warren et al., Ann. Rev. Immunol., 4:369 [1986]; Gupta et al., Vaccine 11:293 [1993]), liposomes (Reddy et al., J. Immunol., 148:1585 [1992]; Rock, Immunol. Today 17:131 [1996]), or, naked or particle absorbed cDNA (Ulmer et al., Science 259:1745 [1993]; Robinson et al., Vaccine 11:957 [1993]; Shiver et al., In: Concepts in Vaccine Development, Kaufmann (ed), p. 423 [1996]; Cease and Berzofsky, Ann. Rev. Immunol., 12:923 [1994]; and Eldridge et al., Sem. Hematol., 30:16 [1993]). Toxin-targeted delivery technologies, also known as receptor mediated targeting, such as those of Avant Immunotherapeutics, Inc. (Needham, Mass.) may also be used.

Vaccine compositions of the invention include nucleic acid-mediated modalities.

DNA or RNA encoding one or more of the peptides of the invention can also be administered to a patient. This approach is described, for instance, in Wolff et. al., Science 247:1465 (1990) as well as U.S. Pat. Nos. 5,580,859; 5,589,466; 5,804,566; 5,739,118; 5,736,524; 5,679,647; WO 98/04720; and in more detail below. Examples of DNA-based delivery technologies include "naked DNA," facilitated (bupivicaine, polymers, peptide-mediated) delivery, cationic lipid complexes, and particle-mediated ("gene gun") or pressure-mediated delivery (See e.g., U.S. Pat. No. 5,922,687).

For therapeutic or prophylactic immunization purposes, the peptides of the invention can be expressed by viral or bacterial vectors. Examples of expression vectors include attenuated viral hosts, such as vaccinia or fowlpox. This approach involves the use of vaccinia virus, for example, as a vector to express nucleotide sequences that encode the peptides of the invention. Upon introduction into an acutely or chronically infected host or into a non-infected host, the recombinant vaccinia virus expresses the immunogenic peptide, and thereby elicits a host CTL and/or HTL response. Vaccinia vectors and methods useful in immunization protocols are described in, e.g., U.S. Pat. No. 4,722,848. Another vector is BCG (Bacille Calmette Guerin). BCG vectors are described in Stover et al., Nature 351:456–460 (1991). A wide variety of other vectors useful for therapeutic administration or immunization of the peptides of the invention, e.g. adeno and adeno-associated virus vectors, retroviral vectors, *Salmonella typhi* vectors, detoxified anthrax toxin vectors, and the like, will be apparent to those skilled in the art from the description herein.

Furthermore, vaccines in accordance with the invention can encompass one or more of the peptides of the invention. Accordingly, a peptide can be present in a vaccine individually. Alternatively, the peptide can be individually linked to its own carrier; alternatively, the peptide can exist as a homopolymer comprising multiple copies of the same peptide, or as a heteropolymer of various peptides. Polymers have the advantage of increased immunological reaction and, where different peptide epitopes are used to make up the polymer, the additional ability to induce antibodies and/or CTLs that react with different antigenic determinants of the pathogenic organism targeted for an immune response. The composition may be a naturally occurring region of an antigen or may be prepared, e.g., recombinantly or by chemical synthesis.

Carriers that can be used with vaccines of the invention are well known in the art, and include, e.g., thyroglobulin, albumins such as human serum albumin, tetanus toxoid, polyamino acids such as poly L-lysine, poly L-glutamic acid, influenza, hepatitis B virus core protein, and the like. The vaccines can contain a physiologically tolerable (i.e., acceptable) diluent such as water, or saline, preferably phosphate buffered saline. The vaccines also typically include an adjuvant. Adjuvants such as incomplete Freund's adjuvant, aluminum phosphate, aluminum hydroxide, or alum are examples of materials well known in the art. Additionally, CTL responses can be primed by conjugating peptides of the invention to lipids, such as tiipalmitoyl-S-glycerylcysteinlyseryl-serine (P3CSS).

Upon immunization with a peptide composition in accordance with the invention, via injection, aerosol, oral, transdermal, transmucosal, intrapleural, intrathecal, or other suitable routes, the immune system of the host responds to the vaccine by initiating a $CD8^+$ T-cell response.

Consequently, the host becomes at least partially immune to later infection, or at least partially resistant to developing an ongoing chronic infection, or derives at least some therapeutic benefit when the antigen was tumor-associated.

In certain embodiments, components that induce T-cell responses are combined with component that induce antibody responses to the target antigen of interest. A preferred embodiment of such a composition comprises Class I and Class II epitopes in accordance with the invention.

For pharmaceutical compositions, the immunogenic peptides of the invention are administered to an individual already infected with HPV. Those in the incubation phase or the acute phase of infection can be treated with the immunogenic peptides separately or in conjunction with other treatments, as appropriate. In therapeutic applications, compositions are administered to a patient in an amount sufficient to elicit an effective $CD8^+$ T-cell response to the virus and to cure or at least partially arrest symptoms and/or complications. An amount adequate to accomplish this is defined as "therapeutically effective dose." Amounts effective for this use will depend on various factors, including but not limited to the peptide composition, the manner of administration, the stage and severity of the disease being treated, the weight and general state of health of the patient, and the judgment of the prescribing physician, but generally range for the initial immunization (that is for therapeutic or prophylactic administration) from about 1.0 ug to about 50,000 ug of peptide for a 70 kg patient, followed by boosting dosages of from about 1.0 ug to about 10,000 ug of peptide pursuant to a boosting regimen over weeks to months depending upon the patient's response and condition by measuring specific $CD8^+$ T-cell activity in the patient's blood.

Immunizing doses followed by boosting doses at established intervals (e.g., from one to four weeks), may be required, possibly for a prolonged period of time to effectively immunize an individual. In the case of chronic infection, administration should continue until at least clinical symptoms or laboratory tests indicate that the viral infection has been eliminated or substantially abated and for a period thereafter.

The pharmaceutical compositions for therapeutic treatment are intended for parenteral, topical, oral or local administration. Preferably, the pharmaceutical compositions are administered parenterally (e.g., intravenously, subcutaneously, intradermally, or intramuscularly). Thus, the invention provides compositions for parenteral administration which comprise a solution of the immunogenic peptides dissolved or suspended in an acceptable carrier, preferably an aqueous carrier. A variety of aqueous carriers may be used, e.g., water, buffered water, 0.9% saline, 0.3% glycine, hyaluronic acid and the like. These compositions may be sterilized by conventional, well known sterilization techniques, or may be sterile filtered. The resulting aqueous solutions may be packaged for use as is, or lyophilized, the lyophilized preparation being combined with a sterile solution prior to administration. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc.

The present invention provides methods for the identification of HPV epitopes in the sequences of various HPV types, as well as the production of peptides which when incorporated into a HPV sequence, are capable of initiating the $CD8^+$ T-cell response.

In some embodiments, the present invention provides methods for the identification of $CD8^+$ T-cell epitopes in HPV sequences and the production of peptides that are capable of initiating the $CD8^+$ T-cell response. In particular, the present invention provides means and compositions suitable for increasing the immunogenicity of HPV epitopes for use in HPV vaccine preparations.

In these embodiments, the present invention provides means for determining the CD8+ T-cell responses of humans against various epitopes comprising a protein of interest. In additional embodiments, once the significant epitopes are identified using the modified I-MUNE® assay system described herein, the significant epitopes are altered to produce epitopes that induce an enhanced immune response to the protein.

Thus, as indicated above, the proteins of the present invention exhibit modified immunogenic responses (e.g., antigenicity and/or immunogenicity) when compared to the native proteins encoded by their precursor DNAs. For example, HPVs that exhibit increased immunogenic responses (e.g., variant HPV epitopes) find use in therapeutic and prophylactic vaccine compositions.

DETAILED DESCRIPTION OF THE INVENTION

The present invention provides means to identify functional $CD8^+$ T-cell epitopes in any protein of interest. The present invention further provides $CD8^+$ T-cell epitopes of various proteins. In some preferred embodiments, the present invention provides $CD8^+$ T-cell epitopes of human papillomavirus (HPV). In additional embodiments, the present invention provides epitopes suitable for use in prophylactic and/or therapeutic vaccines. In particularly preferred embodiments, the present invention provides modified epitopes suitable for use in prophylactic and/or therapeutic vaccines.

During the development of the present invention, it was determined that the addition of anti-CD40 antibody to the test system provided a means to assess the $CD8^+$ T-cell response to various peptides. Although it is not intended that the present invention be limited to any particular mechanism, it is believed that the inclusion of anti-CD40 antibody mimics the CD40 ligand on activated $CD4^+$ T-cells. This attaches to the CD40 receptor present on the surfaces of APCs (e.g., dendritic cells) and stimulates the activation of relevant $CD8^+$ T-cells through increased MHC and B7 expression.

In preliminary experiments, anti-CD40 antibody was tested in the I-MUNE® assay system with HLA-A2 restricted peptides. No responses were observed when anti-CD40 antibody was not used. In contrast, significant improvement in the responses was observed when anti-CD40 was added. In these early experiments, five concentrations of anti-CD40 were tested (10 ug/ml, 5 ug/ml, 2 ug/ml, 1 ug/ml, and 0.5 ug/ml). The 10 ug/ml concentration was determined to be too high, as it killed the cells. The 0.5 ug/ml concentration was a bit too low, although it did work in cases where the cell donor had background values that were higher than usual. Thus, six comparisons were conducted using the 5 ug/ml, 2 ug/ml, and 1 ug/ml concentrations. Statistical analysis of the results was performed, using Stat-Ease DX6.1 software (Stat-Ease, Inc., Minneapolis, Minn.). Based on these results, the 1 ug/ml concentration was chosen, as it resulted in the highest proliferation response compared to the background. The 1 ug/ml concentration also helps keep the background lower in comparison to 2.5 ug/ml and 5 ug/ml, allowing more responses to be detected. Nonetheless, it is contemplated that in other assay systems, different antibody concentrations will find use.

The present invention further provides $CD8^+$ T-cell epitopes in E7 proteins from two strains of human papillomavirus (HPV). In some preferred embodiments, the present invention provides means for the development of HPV vaccines, in particular multivalent vaccines for the prevention of infection with high-risk HPV strains. In additional embodiments, the present invention provides means for the development of therapeutic vaccines against high-risk HPV types suitable for use in the prevention of the development of benign and/or malignant tumors in infected individuals. The present invention further provides epitopes suitable for use in prophylactic and/or therapeutic vaccines. In particularly preferred embodiments, the present invention provides modified epitopes suitable for use in prophylactic and/or therapeutic vaccines.

E7 oncoprotein from HPV represents an especially attractive targets for a DNA vaccine because of its ubiquitous expression in cervical carcinoma cases. E7 protein and E6 protein are responsible for the oncogenic characteristics of HPV (Finzer et al., Cancer Lett., 188:15–24 [2002]). Continued expression of these two proteins is necessary for continued proliferation and survival of cervical cancer cells (von Knebel-Doeberitz et al., Cancer Res., 48:3780–6 [1988]). E6 and E7 are responsible for transformation in cervical lesions and inhibition of apoptosis. Several studies have indicated that immunological responses against these proteins can be protective against cervical cancer. Natural CTL responses to E6 and E7 have been shown to be more common in HPV16 positive women without squamous intraepithelial neoplasia (SIL) than in HPV 16 positive women with SIL (Nakagawa et al., J. Infect. Dis., 175: 927–931 [1997]). In addition, cell-mediated immune responses to specific protective peptides of E6 and E7 have been correlated with disease regression and resolution of viral infection (Kadish et al., Cancer Epidemiol. Biomarkers Prev., 11:483–488 [2002]). Furthermore, vaccination with E7 DNA has been demonstrated to be highly efficient at eliciting cytotoxic T-cell response (Osen et al., Vaccine 19:4276–4286 [2001]).

The present invention, in which an epitope vaccine is used rather than a full-length vaccine, is attractive because it obviates the concern of administering an oncogenic product. Also, because of size constraints of a DNA vaccine, inclusion of only immunogenic regions of E7 allows for the coverage of more high risk strains. Patients with HPV infections often carry more than one HPV strain, and individuals who clear an HPV infection of one strain can become re-infected with a second strain. Although CTL epitopes are typically associated with antiviral vaccines, there are several reasons for including CD4+ epitopes in conjunction with CD8+ epitopes in some preferred embodiments of the present invention. For example, antigen-specific CD4+ help is generally required for activation of CD8+ cytolytic activity through cross-priming of antigen presenting cells (See, Bennett et al., Nature 393:478–480 [1998]; Schoenberger et al., Nature 393:480–483 [1998]; and Ridge et al., Nature 393:474–478 [1998]). Furthermore, studies in animal models have demonstrated that vaccines that include both CD4 and CD8 epitopes derived from the same antigen induce a strong protective response (See, Ossendrop et al., J. Exp. Med., 187:693–702 [1998]; De Veermann et al., J. Immunol., 162: 144–151 [1999]; and Zwaveling et al., J. Immunol., 169:350–8 [2002]).

In some preferred embodiments, the present invention provides compositions and methods for the development of vaccine compositions directed against HPV strains, in particular those associated with higher risks of malignancy. Thus, in some particularly preferred embodiments, the present invention provides compositions and methods for the development of vaccine compositions directed against the E7 proteins of two high risk HPV strains (i.e., strains 16 and 18). Importantly, the presence of DNA from these HPV strains has been associated with cervical lesions and cancers (Lorincz et al., Obstet Gynecol., 79:328–337. [1992]). As described in co-pending U.S. patent application Ser. No. 60/466,235, filed, Apr. 28, 2003, MHC Class II helper epitopes in E6 and E7 proteins of various high risk and moderate risk HPV strains were identified. Thus, in addition to the help epitopes previously described, it is contemplated that the compositions and methods involving CD8+ epitopes of the present invention will find use therapeutic and/or preventative vaccine compositions.

EXPERIMENTAL

The following examples are provided in order to demonstrate and further illustrate certain preferred embodiments and aspects of the present invention and are not to be construed as limiting the scope thereof.

In the experimental disclosure which follows, the following abbreviations apply: M (molar); mM (millimolar); µM (micromolar); nM (nanomolar); mol (moles); mmol (millimoles); µmol (micromoles); nmol (nanomoles); gm (grams); mg (milligrams); µg (micrograms); pg (picograms); L (liters); ml (milliliters); µl (microliters); cm (centimeters); mm (millimeters); µm (micrometers); nm (nanometers); ° C. (degrees Centigrade); cDNA (copy or complimentary DNA); DNA (deoxyribonucleic acid); ssDNA (single stranded DNA); dsDNA (double stranded DNA); dNTP (deoxyribonucleotide triphosphate); RNA (ribonucleic acid); HRP (horseradish peroxidase); AEC substrate (solution of sodium acetate, dimethylsulfoxide, methanol and urea peroxide); AEC chromogen (solution of 3-amino-9-ethylcarbazole (2% w/v), and N,N-dimethylformamide; (PBS (phosphate buffered saline); g (gravity); DC (dendritic cell); PHA (phytohemagglutinin); OD (optical density); Dulbecco's phosphate buffered solution (DPBS); HEPES (N-[2-Hydroxyethyl]piperazine-N-[2-ethanesulfonic acid]); HBS (HEPES buffered saline); SDS (sodium dodecylsulfate); Tris-HCl (tris[Hydroxymethyl]aminomethane-hydrochloride); DMSO (dimethyl sulfoxide); EGTA (ethylene glycol-bis(β-aminoethyl ether) N,N, N',N'-tetraacetic acid); EDTA (ethylenediaminetetracetic acid); DPBS (Dulbecco's phosphate buffered solution); bla (β-lactamase or ampicillin-resistance gene); Endogen (Endogen, Woburn, Mass.); CytoVax (CytoVax, Edmonton, Canada); Wyeth-Ayerst (Wyeth-Ayerst, Philadelphia, Pa.); NEN (NEN Life Science Products, Boston, Mass.); Wallace Oy (Wallace Oy, Turku, Finland); Pharma AS (Pharma AS, Oslo, Norway); Dynal (Dynal, Oslo, Norway); Bio-Synthesis (Bio-Synthesis, Lewisville, Tex.); Mimotopes (Mimotopes, Inc., San Diego, Calif.); ATCC (American Type Culture Collection, Rockville, Md.); Gibco/BRL (Gibco/BRL, Grand Island, N.Y.); Sigma (Sigma Chemical Co., St. Louis, Mo.); Pharmacia (Pharmacia Biotech, Pisacataway, N.J.); Invitrogen (Invitrogen, Inc., Grand Island, N.Y.); Abbott (Abbott Laboratories, Abbott Park, Ill.); List (List Biological Laboratories Inc., Campbell, Calif.); Perkin Elmer (PerkinElmer Life Sciences, Boston Mass.); eBioscience (eBioscience, San Diego, Calif.); BD Bioscience (BD Bioscience); Cellular Technology (Cellular Technology, Cleveland, Ohio); and Stratagene (Stratagene, La Jolla, Calif.).

EXAMPLE 1

Preparation of E7 Epitopes

Full length amino acid sequences of E7 proteins from HPV 16, and 18, were used to create 9-merpeptide sets. SwissProt. PO3129 corresponds to HPV16 E7. SwissProt. P06788 corresponds to HPV18 E7. These variant peptides were synthesized by Mimotopes, using the multi-pin synthesis technique known in the art (See e.g., Maeji et al., J. Immunol. Meth., 134:23–33 [1990]). The 9-mer peptides were created such that sequences with adjacent peptides shared 8 amino acids (i.e., each peptide was offset by one amino acid). Peptides were diluted with DMSO to provide a stock concentration of approximately 2 mg/ml. The final concentration of peptides used in each assay was 5 µg/ml.

EXAMPLE 2

Preparation of Cells Used in the Assay System for the Identification of Peptide T-Cell Epitopes in HPV Using Human T-Cells Fresh human peripheral blood cells were collected from humans of unknown exposure status to HPV. These cells were tested to determine antigenic epitopes in HPV 16 and 18, as described in Example 3.

Peripheral mononuclear blood cells (stored at room temperature, no older than 24 hours) were prepared for use as follows. PBMC's were isolated from buffy coat material by centrifuging over an underlay of Lymphoprep at 1000×g for 30 minutes. The interface layer was collected and washed and counted using the Cell-Dyn 3700 System (Abbott). Then, suspensions containing $10^8$ PBMC's resuspended in 30 ml of AIM-V (Invitrogen) were prepared and then allowed to adhere to plastic T-75 culture flasks for two hours. The remainder of the cells were frozen at $5\times10^7$ cells/ml in 45% FCS (Gibco/BRL), 45% PBS w/o Ca & Mg (Mediatech), and 10% DMSO (Sigma). After the two hour PBMC incubation, non-adherent cells were removed from the flasks. The adherent cells were cultured in the flasks with 800 units/ml recombinant human GM-CSF (R&D Systems) and 100 units/ml recombinant human IL-4 (Endogen) at 37° C., 5% $CO_2$. On day 5 of incubation, 50 units/ml recombinant human I1-1α (Endogen) and 0.2 units/ml recombinant human TNF-α were added to the cultures. Adherent and non-adherent dendritic cells were harvested, washed, and counted on day 7, following a one-hour treatment with 30 mg/ml mitomycin C (Sigma) and 10 mM EDTA.

Autologous CD8+ T-cells were prepared from frozen aliquots of PBMCs. After thawing and washing in DPBS, CD8+ T-cells were isolated using a commercially available CD8 negative selection kit (Dynal), according to the manufacturer's instructions. Cells were counted using the Abbott Cell-Dyn 3700 System. The purity obtained using these methods was generally found to be greater than 90%.

EXAMPLE 3

T-Cell Proliferation Assays

This Example describes the assay system used in the present invention. The basic test system is also referred to as the "I-MUNE®" assay system. The basic I-MUNE® assay system was modified as described herein to facilitate analysis of CD8+ T-cell responses. As described in greater detail below, the modifications used in the development of the present invention involved the use of CD8 negative selection beads on PBMC (i.e., instead of CD4). In addition, when CD8 cells were resuspended, between $1.5 \times 10^5$ ml and $2.5 \times 10^5$ ml of a 2 ug/ml anti-CD40 solution was added, before placing the DCs and peptides in the plates (the final concentration of anti-CD40 was 1 ug/ml); and 1 ul of 1 ug/ml PHA was used as a positive control, instead of tetanus toxoid.

In 96-well, round bottom plates, autologous dendritic cells and CD8+ T-cells were combined with test peptides. More specifically, in a volume of 100 μl/well, $2 \times 10^4$ dendritic cells in AIM V were combined with individual peptides (at a final peptide concentration of 5 μg/ml and a final DMSO concentration of 0.25%). After a one-hour incubation at 37° C., 5% $CO_2$, $2 \times 10^5$ CD8+ T-cells with 2 μg/ml anti-CD40 (eBioscience; Clone 5C3 mouse IgG1, kappa) were added to the culture for a total volume of 200 μl and a final anti-CD40 concentration of 1 μg/ml per well. Negative control wells contained dendritic cells, CD8+ T-cells and 0.25% DMSO. Positive control wells contained dendritic cells, CD8+ T-cells (at the same concentrations as the test wells) and 0.25% DMSO with 5 μg/ml PHA (Sigma) (List). In some experiments, 1 ug/ml anti-IgG1 (eBioscience; Clone P3 mouse IgG1, kappa) was used as an isotype control for comparison purposes. Individual peptides were tested in duplicate or triplicate for each donor.

Figure 3:
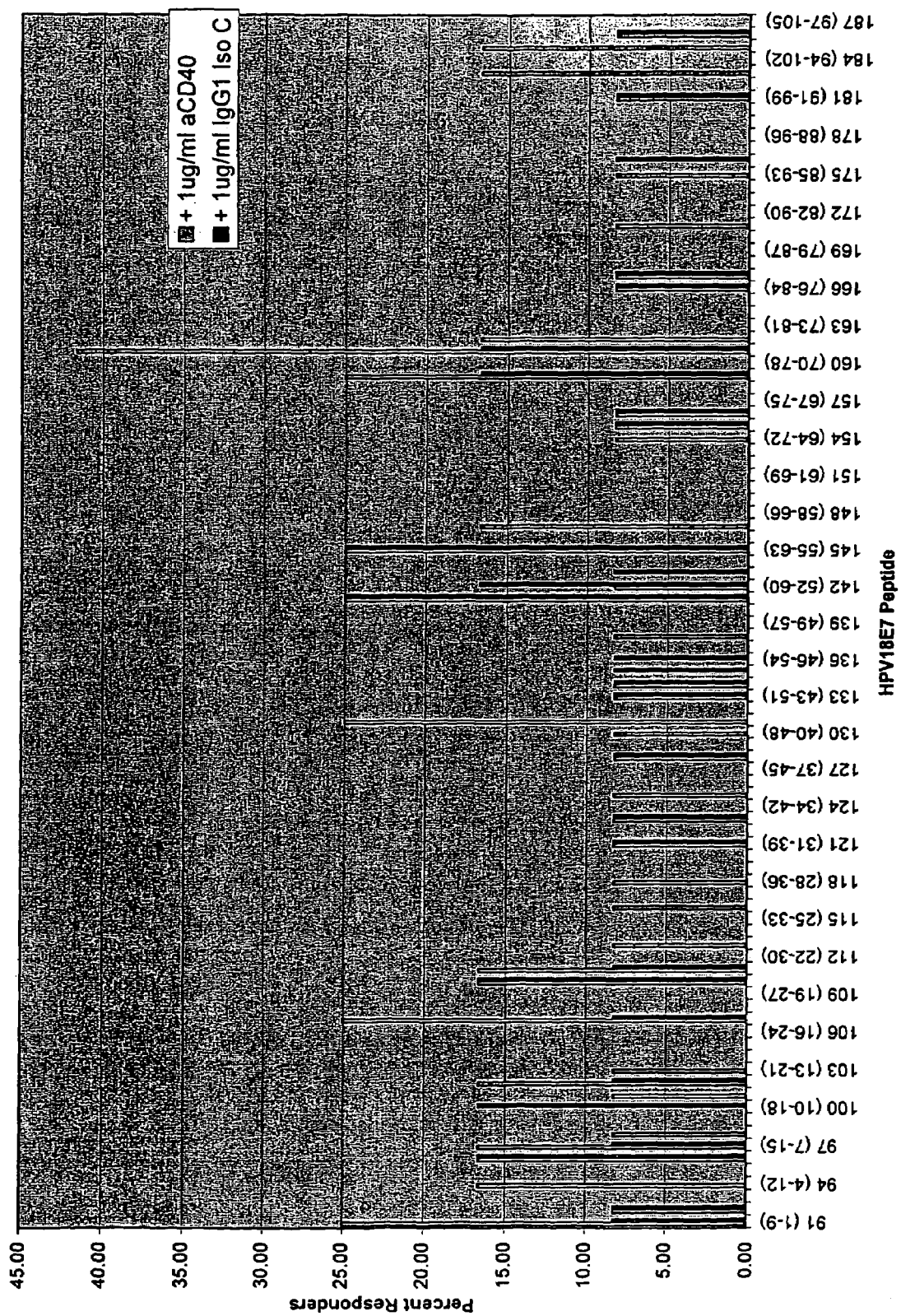

After 5 days of incubation at 37° C., 5% $CO_2$, the cultures were pulsed with 0.25 μCi/well tritiated thymidine (Perkin Elmer). After a subsequent 24 hours of incubation, plates were harvested and assessed for incorporation of the tritiated thymidine (i.e., T-cell proliferation) using a Wallac Microbeta TriLux liquid scintillation counter (Perkin Elmer). Responses were averaged over the duplicate tests performed for each specimen. Positive responses were defined as having a response at least 2.95 times the background. Based on results obtained with the anti-CD40 antibody and the anti-IgG1 isotype antibody, the effect of anti-CD40 was found to be specific (See, FIG. 3).

A set of data was accumulated for both proteins tested with at least 45 donors. The percent response rate for each peptide was determined for the entire population of donors.

In this assay system, the "mean background response rate for a population of donors" is defined as the average percent response rate for all the peptides in a set. In this assay system, a "major epitope" is defined as having a response rate at least three standard deviations above the mean background response rate. "Moderate epitopes" are those epitopes that produce results that are at least two standard deviations above the mean or three times the background. "Minor epitopes" are those that have a response rate that is at least twice the background value. As described herein, this assay identified several epitopes in both of the HPV strains tested.

A. HPV E7.16

For this antigen, 45 donors were tested in the I-MUNE® assay to determine epitopes for HPV E7.16. FIG. 1 provides a graph showing the responses to each epitope. Also as indicated in Table 1, there were 19 epitopes of interest identified in this antigen.

TABLE 1

HPV E7.16 Epitopes of Interest

| Peptide Number | Epitope Classification | Epitope Sequence | SEQ ID NO: |
|---|---|---|---|
| 1 | Minor | MHGDTPTLH | SEQ ID NO: 1 |
| 4 | Moderate | DTPTLHEYM | SEQ ID NO: 2 |
| 5 | Minor | TPTLHEYML | SEQ ID NO: 3 |
| 7 | Minor | TLHEYMLDL | SEQ ID NO: 4 |
| 8 | Minor | LHEYMLDLQ | SEQ ID NO: 5 |
| 9 | Minor | HEYMLDLQP | SEQ ID NO: 6 |
| 12 | Minor | MLDLQPETT | SEQ ID NO: 7 |
| 21 | Major | DLYCYEQLN | SEQ ID NO: 8 |
| 36 | Moderate | DEIDGPAGO | SEQ ID NO: 9 |
| 43 | Minor | GQAEPDRAH | SEQ ID NO: 10 |
| 54 | Minor | IVTFCCKCD | SEQ ID NO: 11 |
| 76 | Minor | IRTLEDLLM | SEQ ID NO: 12 |
| 79 | Minor | LEDLLMGTL | SEQ ID NO: 13 |
| 80 | Minor | EDLLMGTLG | SEQ ID NO: 14 |
| 81 | Minor | DLLMGTLGI | SEQ ID NO: 15 |
| 82 | Minor | LLMGTLGIV | SEQ ID NO: 16 |
| 83 | Minor | LMGTLGIVC | SEQ ID NO: 17 |
| 84 | Minor | MGTLGIVCP | SEQ ID NO: 18 |
| 89 | Minor | IVCPICSQK | SEQ ID NO: 19 |

B. HPV E7.18

Figure 2:
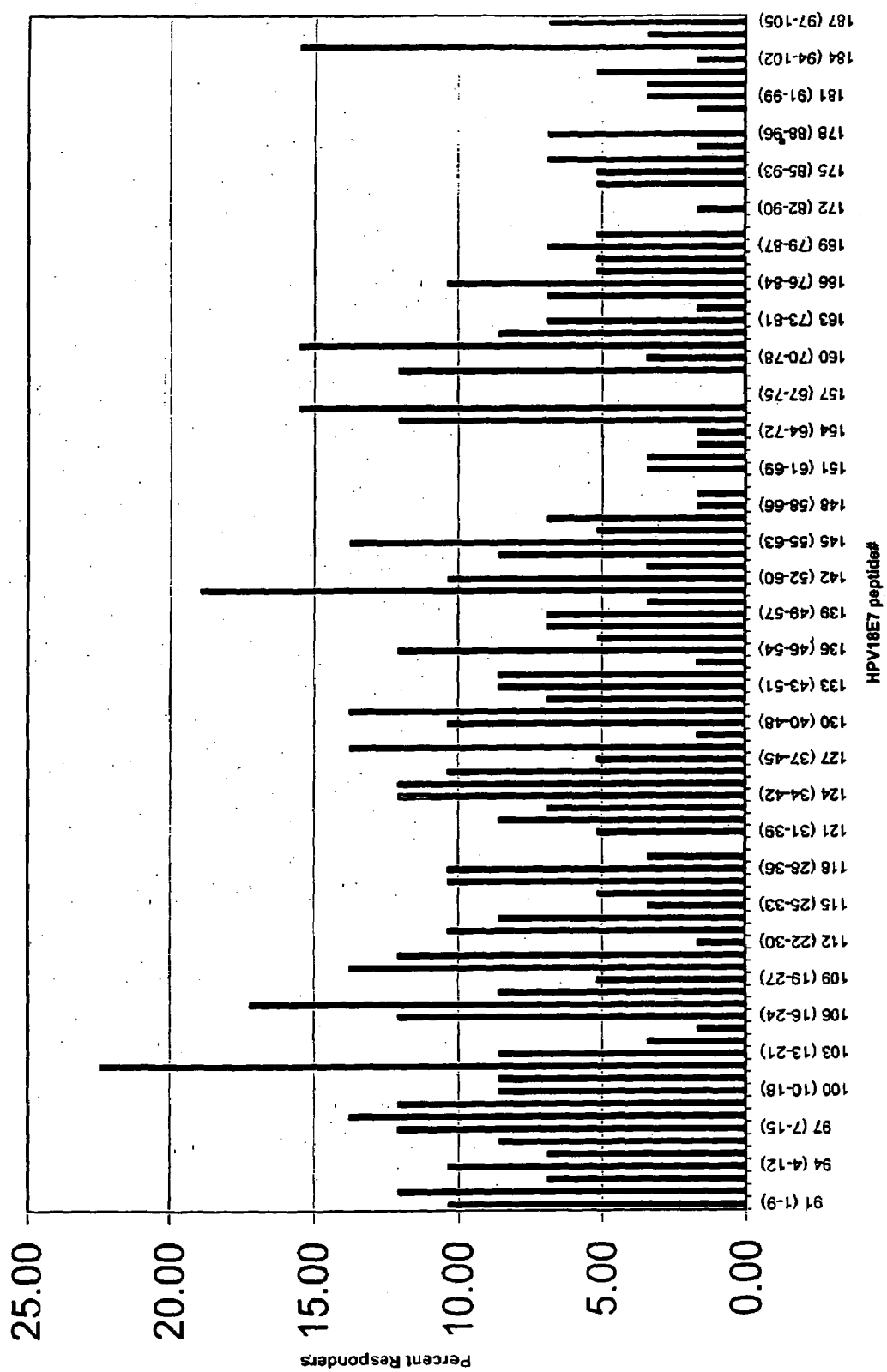

For this antigen, 58 donors were tested in the I-MUNE® assay to determine the epitopes of interest for HPV E7.18. FIG. 2 provides a graph showing the responses to each epitope. Also as indicated in Table 2, there were 6 epitopes of interest identified in this antigen.

TABLE 2

HPV E7.18 Epitopes of Interest

| Peptide Number | Epitope Classification | Epitope Sequence | SEQ ID NO: |
|---|---|---|---|
| 12 | Major | VLHLEPQNE | SEQ ID NO: 20 |
| 17 | Minor | PQNEIPVDL | SEQ ID NO: 21 |
| 51 | Minor | ARRAEPQRH | SEQ ID NO: 22 |
| 66 | Minor | CKCEARIKL | SEQ ID NO: 23 |
| 71 | Minor | RIKLVVESS | SEQ ID NO: 24 |
| 95 | Minor | SFVCPWCAS | SEQ ID NO: 25 |

The results shown above provide the epitopes of interest in HPV16 and HPV 18 E7 proteins. Thus, the present invention not only provides means to assess CD8+ T-cell responses to epitopes of a protein of interest, but also provides epitopes that are suitable for modification and use in such compositions as vaccines.

EXAMPLE 4

INF-γ ELISPOT Assays

In this Example, ELISPOT (BD Biosciences) assays were used to determine whether epitopes identified in the previous Examples were effector epitopes. In these experiments, INF-γ ELISPOT assays were run with epitopes identified as described above, along with low and non-responder peptides from the HPV18 E7 pepset. These assays were tested in parallel with the CD8+ I-MUNE® epitope mapping assay for 20 donors.

In these experiments, CD8⁺ T cells and dendritic cells were plated in round-bottom 96-well format plates at 100 μL of each cell mix per well. Each peptide of interest was added to the wells at a final concentration of 5 μg/ml in 0.25% DMSO. The control wells contained DMSO, but did not contain peptide. Anti-human CD40 Ab (eBioscience) was added at 1 μg/ml per well. Each peptide was tested in duplicate. Cultures were incubated at 37° C., 5% $CO_2$ for 5 days.

On day 5 of incubation, the cells were resuspended by pipetting and the cell suspensions were transferred into an ELISPOT (BD Biosciences) plate, pre-coated with purified α-human IFN-γ capture antibody. Plates were incubated at 37° C., 5% $CO_2$ for 24 hours. The plates were washed and then incubated for two hours with biotinylated α-human IFN-γ detection antibody. Avidin-HRP and AEC substrate and chromogen were used for spot development. Spots were quantified using an ImmunoSpot® analyzer (Cellular Technology), as per the manufacturer's directions. Positive responses were defined as those being at least three times above the background level.

Figure 4:
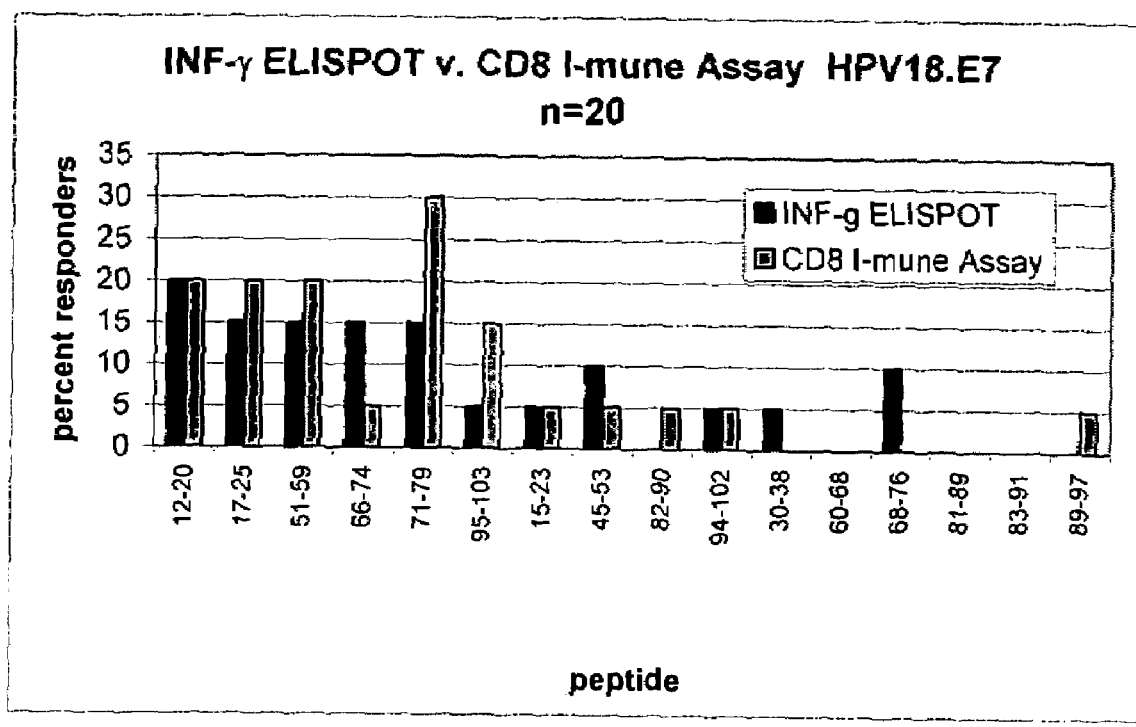

The compiled results are provided in FIG. 4. As indicated in this Figure, there was a strong correlation between INF-γ production and proliferation for the epitopes (r=0.67; p=0.0019). This correlation between INF-γ secretion and CD8+ T-cell proliferation sufficiently shows that the proliferating CD8+ T-cells are indeed effector cells. Comparison of CD8+ proliferation with INF-γ production indicates that the epitopes found are effector epitopes. Therefore, the CD8+ proliferation in the I-MUNE® assay is of effector cells, rather than anergic cells.

As indicated, there were a few peptides where there were more positive for INF-γ than for proliferation. It is not an uncommon phenomenon to have cytokine production without proliferation, especially as a memory cell response. In the cases where proliferation without INF-γ production was observed, INF-γ was detected at twice the background level, but this did not meet the established criteria of a "positive" in the development of the present invention. However, this could be considered by many other researchers as a positive. In sum, the results provided here demonstrate that epitopes identified with the I-MUNE® assay can be verified for CTL activity through commercially available assay systems such as the INF-γ ELISPOT assay.

We claim:

1. A method for determining a CD8+ T-cell epitope in a protein, comprising the steps at:
   (a) obtaining from a solution of dendritic cells and a solution of naive CD8+ T-cells from a single human blood source;
   (b) differentiating said dendritic cells, in said solution of dendritic cells, to produce a solution of differentiated dendritic cells;
   (c) preparing a pepset of peptides from said protein, wherein said pepset comprises said T-cell epitope;
   (d) combining said solution of said CD8+ T-cells and anti-CD40 antibody to provide a T-cell and antibody solution,
   (e) exposing said differentiated dendritic cells and said pepset to said T-cell and antibody solution; and
   (f) measuring the proliferation of said T-cells in said step (a).

2. The method of claim 1, wherein said protein is selected from the group consisting of virus proteins, baterial proteins, parasitic proteins, fungal proteins, and tumor-related proteins.

* * * * *